US009861328B2

(12) United States Patent
Kang et al.

(10) Patent No.: US 9,861,328 B2
(45) Date of Patent: Jan. 9, 2018

(54) MOBILE X-RAY IMAGING APPARATUS AND CONTROL METHOD FOR THE SAME

(71) Applicants: SAMSUNG ELECTRONICS CO., LTD., Suwon-si (KR); SAMSUNG LIFE PUBLIC WELFARE FOUNDATION., Seoul (KR)

(72) Inventors: Dong Goo Kang, Suwon-si (KR); Young Hun Sung, Hwaseong-si (KR); Myung Jin Chung, Seoul (KR)

(73) Assignees: SAMSUNG ELECTRONICS CO., LTD., Suwon-si (KR); SAMSUNG LIFE PUBLIC WELFARE FOUNDATION, Seoul (KR)

( * ) Notice: Subject to any disclaimer, the term of this patent is extended or adjusted under 35 U.S.C. 154(b) by 445 days.

(21) Appl. No.: 14/196,447

(22) Filed: Mar. 4, 2014

(65) Prior Publication Data
US 2014/0247918 A1 Sep. 4, 2014

(30) Foreign Application Priority Data
Mar. 4, 2013 (KR) .................... 10-2013-0023018

(51) Int. Cl.
*A61B 6/08* (2006.01)
*A61B 6/00* (2006.01)

(52) U.S. Cl.
CPC .......... *A61B 6/4405* (2013.01); *A61B 6/4452* (2013.01); *A61B 6/4458* (2013.01); *A61B 6/547* (2013.01); *A61B 6/4464* (2013.01)

(58) Field of Classification Search
CPC ......... A61B 5/0059; A61B 5/066; A61B 6/44; A61B 6/4405; A61B 6/4411; A61B 6/4447; A61B 6/4452; A61B 6/4458
(Continued)

(56) References Cited

U.S. PATENT DOCUMENTS 7,211,803 B1 5/2007 Dhurjaty et al.
2004/0105526 A1* 6/2004 Zhang .................. A61B 6/08
378/205
(Continued)

FOREIGN PATENT DOCUMENTS

DE 102010008552 A1 8/2011
JP 2005-270277 A 10/2005
(Continued)

OTHER PUBLICATIONS

Communication, dated Jun. 30, 2014 issued by the European Patent Office in counterpart Patent Application No. 14157585.2.
(Continued)

*Primary Examiner* — Jason McCormack
(74) *Attorney, Agent, or Firm* — Sughrue Mion, PLLC

(57) ABSTRACT

A mobile X-ray imaging apparatus and method of controlling the same, the mobile X-ray imaging apparatus including a movable main body, an X-ray source installed on the main body via an arm, a tilt angle and rotation angle of the arm being adjustable, a portable X-ray detector configured to detect X-rays emitted from the X-ray source, a position information acquirer configured to acquire position information indicating a position of the X-ray source relative to the portable X-ray detector, and a position controller configured to control the X-ray source to move to a position corresponding to the portable X-ray detector based on the acquired position information.

13 Claims, 32 Drawing Sheets

(58) Field of Classification Search
USPC .................................... 378/205, 193, 167
See application file for complete search history.

(56) References Cited

U.S. PATENT DOCUMENTS

| | | | |
|---|---|---|---|
| 2006/0109958 A1* | 5/2006 | Ertel | A61B 6/08 378/205 |
| 2009/0028290 A1* | 1/2009 | Grebner | A61B 6/4014 378/9 |
| 2012/0002784 A1* | 1/2012 | Nishino | A61B 6/4216 378/62 |
| 2012/0207274 A1 | 8/2012 | Yang et al. | |
| 2013/0083894 A1* | 4/2013 | Niebler | A61B 6/4441 378/62 |

FOREIGN PATENT DOCUMENTS

| | | | |
|---|---|---|---|
| JP | 2010240247 A | 10/2010 | |
| JP | 2011125544 A | 6/2011 | |

OTHER PUBLICATIONS

Communication dated Feb. 2, 2017, issued by the European Patent Office in counterpart European application No. 14157585.2.

* cited by examiner (a)

(b)

MOBILE X-RAY IMAGING APPARATUS AND CONTROL METHOD FOR THE SAME

CROSS-REFERENCE TO RELATED APPLICATION(S)

This application claims the benefit of Korean Patent Application No. 10-2013-0023018, filed on Mar. 4, 2013 in the Korean Intellectual Property Office, the disclosure of which is incorporated herein by reference in its entirety.

BACKGROUND

1. Field

Exemplary embodiments of the present disclosure relate to a mobile X-ray imaging apparatus for generating an X-ray image by passing X-rays through an object and a control method therefor.

2. Description of the Related Art

X-ray imaging apparatuses are non-invasive diagnostic apparatuses for acquiring an image of the internal structure of an object by irradiating the object with X-rays and detecting X-rays having passed through the object.

In general, X-ray imaging apparatuses, which include an X-ray source and an X-ray detector, are fixed in a certain space, and thus, to perform X-ray imaging, it is necessary for a patient to move to an inspection room where an X-ray imaging apparatus is installed and adjust his or her body to a position corresponding to the X-ray imaging apparatus.

However, it is difficult to perform X-ray imaging using a general X-ray imaging apparatus for patients who have problems walking, and thus, mobile X-ray imaging apparatuses capable of performing X-ray imaging in many places have been developed.

Mobile X-ray imaging apparatuses use X-ray sources installed at a movable main body and portable X-ray detectors, and thus can directly perform X-ray imaging of patients who have problems walking.

However, in a mobile X-ray imaging apparatus, both an X-ray source and an X-ray detector are freely movable in 3D space, and thus it is difficult to identify relative positions thereof and to align the relative positions with respect to each other.

SUMMARY

Therefore, it is an aspect of the exemplary embodiments to provide a mobile X-ray imaging apparatus and a control method therefor in which accuracy of position alignment of an X-ray source and a portable X-ray detector may be increased by identifying position information of the X-ray source relative to the portable X-ray detector which are being freely used in 3D space, and automatically controlling the position of the X-ray source based on the identified position information or providing a user with the position information.

It is another aspect of the exemplary embodiments to provide a mobile X-ray imaging apparatus and a control method therefor in which an exposure amount of X-rays is effectively controlled by determining image parameters applied to X-ray imaging based on identified position information, and excellent image quality may be acquired.

Additional aspects will be set forth in part in the description which follows and, in part, will be obvious from the description, or may be learned by practice of the exemplary embodiments.

In accordance with an aspect of an exemplary embodiment, there is provided a mobile X-ray imaging apparatus including a movable main body, an X-ray source installed on the main body via an arm, at least one from among a tilt angle and a rotation angle of the arm being adjustable, a portable X-ray detector configured to detect X-rays emitted from the X-ray source, a position information acquirer configured to acquire position information indicating a position of the X-ray source relative to the portable X-ray detector, and a position controller configured to control the X-ray source to move to a position corresponding to the portable X-ray detector based on the position information.

In accordance with another aspect of an exemplary embodiment, there is provided a mobile X-ray imaging apparatus including an X-ray source installed on a movable main body to be movable, a portable X-ray detector configured to detect X-rays emitted from the X-ray source, a position information acquirer configured to acquire position information indicating a position of the X-ray source relative to the portable X-ray detector based on a movement of the X-ray source, and a position information supplier configured to provide a user with the acquired position information.

In accordance with another aspect of an exemplary embodiment, there is provided a mobile X-ray imaging apparatus including an X-ray source installed at a movable main body to be movable, a portable X-ray detector configured to detect X-rays emitted from the X-ray source, a position information acquirer configured to acquire position information indicating a position of the X-ray source relative to the portable X-ray detector when the X-ray source and the portable X-ray detector are located at positions for X-ray imaging, and a parameter determiner configured to determine an image parameter to be applied for the X-ray imaging based on the acquired position information.

In accordance with another aspect of an exemplary embodiment, there is provided a method of controlling a mobile X-ray imaging apparatus including an X-ray source installed on a movable main body via an arm, a tilt angle and rotation angle of the arm being adjustable, and a portable X-ray detector configured to detect X-rays emitted from the X-ray source includes sensing a position of the portable X-ray detector, acquiring position information indicating a position of the X-ray source relative to the portable X-ray detector based on sensing results of the sensing, and controlling the X-ray source to move to a position corresponding to the portable X-ray detector based on the acquired position information.

In accordance with another aspect of an exemplary embodiment, there is provided a method of controlling a mobile X-ray imaging apparatus comprising an X-ray source installed on a movable main body and a portable X-ray detector configured to detect X-rays emitted from the X-ray source includes sensing a position of the portable X-ray detector, acquiring in real time position information indicating a position of the X-ray source relative to the portable X-ray detector based on the sensing results of the sensing, and providing a user with the real-time acquired position information.

In accordance with a further aspect of an exemplary embodiment, there is provided a method of controlling a mobile X-ray imaging apparatus comprising an X-ray source installed on a movable main body and a portable X-ray detector configured to detect X-rays emitted from the X-ray source includes sensing a position of the portable X-ray detector when the X-ray source and the portable X-ray detector are located at positions for X-ray imaging, acquiring position information indicating a position of the X-ray source relative to the portable X-ray detector based on the sensing results of the sensing, and determining an image parameter to be applied for the X-ray imaging based on the acquired position information.

BRIEF DESCRIPTION OF THE DRAWINGS

These and/or other aspects of the exemplary embodiments will become apparent and more readily appreciated from the following description of the exemplary embodiments, taken in conjunction with the accompanying drawings in which.

DETAILED DESCRIPTION

Figure 1A:
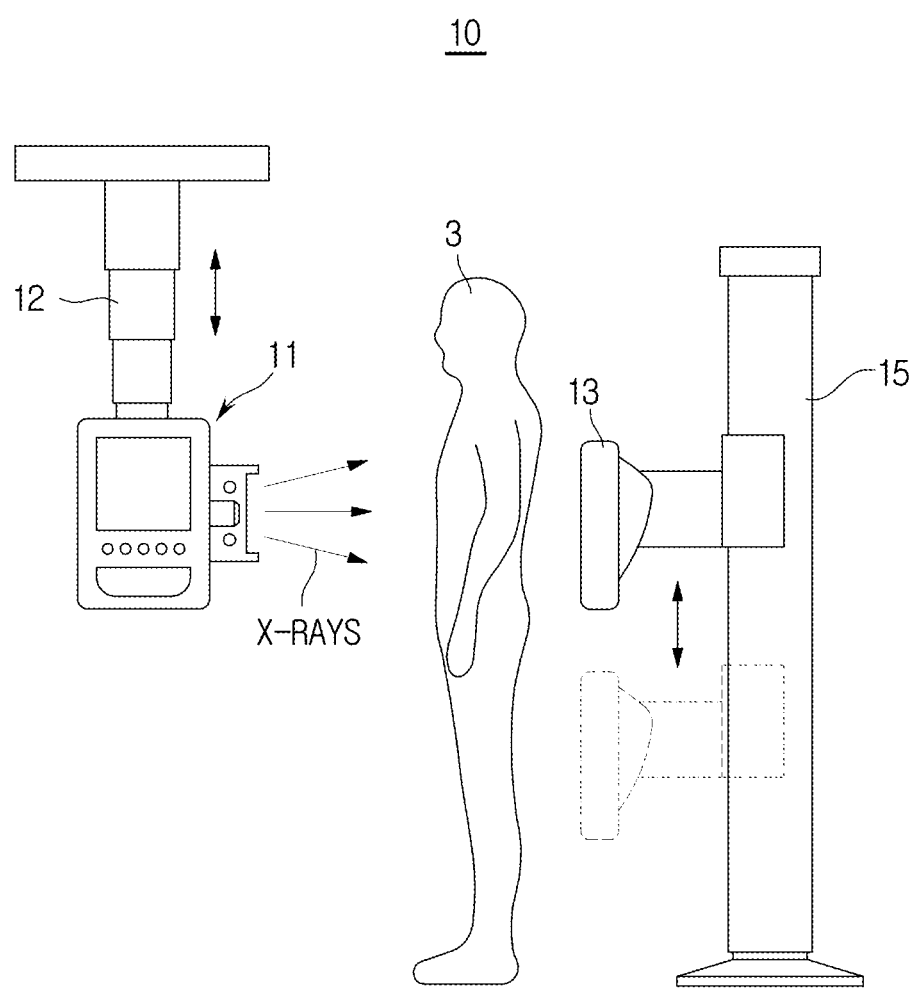
FIG. 1A is an exterior view of a general X-ray imaging apparatus.

Reference will now be made in detail to the exemplary embodiments, examples of which are illustrated in the accompanying drawings, wherein like reference numerals refer to like elements throughout.

Hereinafter, exemplary embodiments of a mobile X-ray imaging apparatus and a control method therefor will be described in detail with reference to the accompanying drawings.

Figure 1B:
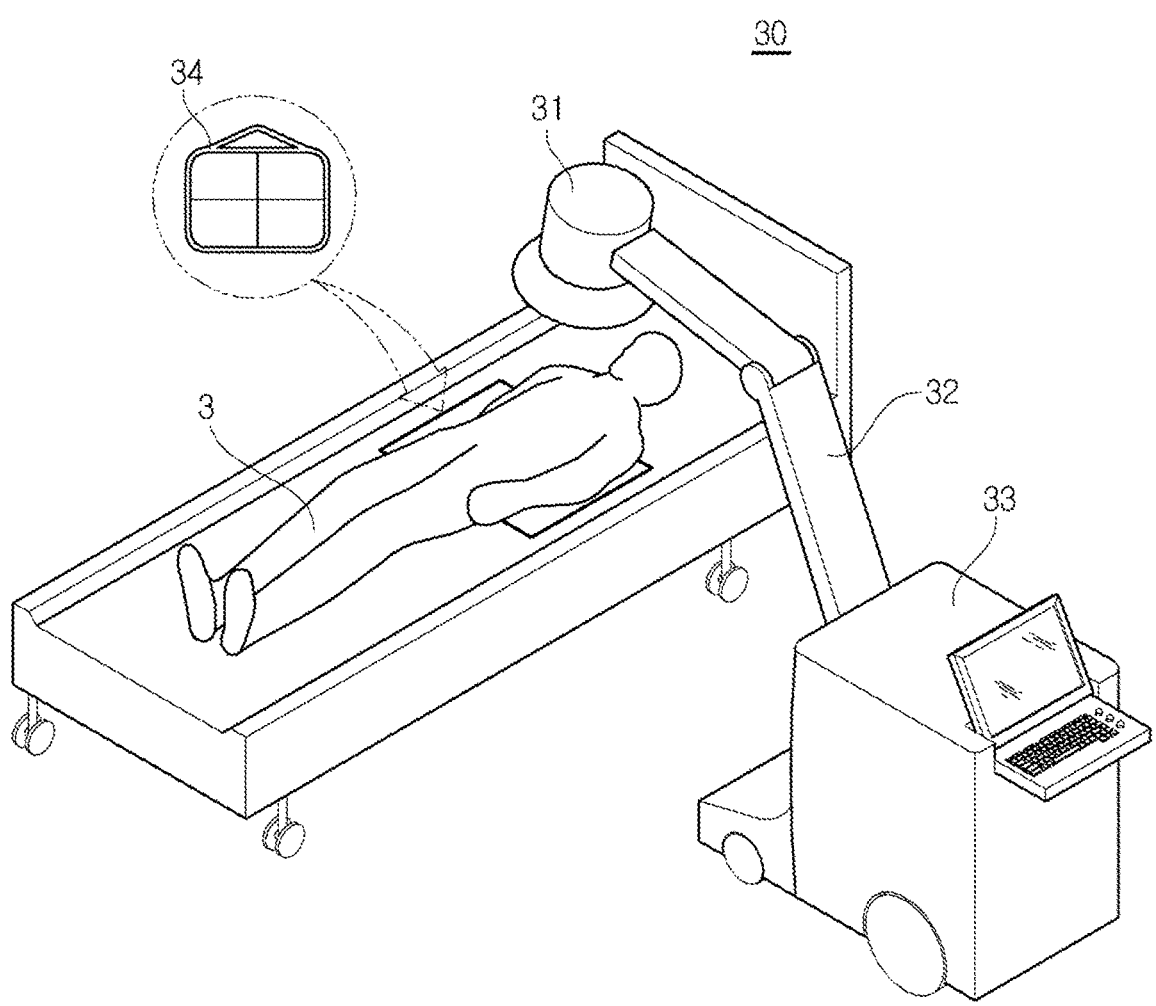
FIG. 1B is an exterior view illustrating an example of a mobile X-ray imaging apparatus.

FIG. 1A is an exterior view of a general X-ray imaging apparatus. FIG. 1B is an exterior view illustrating an example of a mobile X-ray imaging apparatus 30.

The general X-ray imaging apparatus includes an X-ray source 11 and an X-ray detector 13 that are fixed in a certain space. For example, as illustrated in FIG. 1A, the X-ray source 11 is connected to an arm 12 installed on the ceiling of an inspection room, and the X-ray detector 13 is connected to a housing 15 fixed on the floor of the inspection room. The arm 12 connected to the X-ray source 11 is extendable and thus the X-ray source 11 is movable in a vertical direction based on the ground, and the X-ray detector 13 is also movable in a vertical direction along the housing 15. That is, in the general X-ray imaging apparatus 10, the X-ray source 11 and the X-ray detector 13 move only in a predetermined direction in a predetermined space.

However, as illustrated in FIG. 1B, in the mobile X-ray imaging apparatus 30, an X-ray source 31 and an X-ray detector 34 may freely move in three-dimensional (3D) space. In particular, the X-ray source 31 may be installed on a main body 33, which is movable, via a support arm 32, and the support arm 32 may be rotatable and have a varying slope so that the X-ray source 31 may freely move. In addition, the mobile X-ray imaging apparatus 30 uses an X-ray detector 34 which is portable and may therefore be placed at a certain position in 3D space.

Thus, it is difficult for a user to identify and control relative positions of the X-ray source 31 and the X-ray detector 34 of the mobile X-ray imaging apparatus 30.

Figure 2:
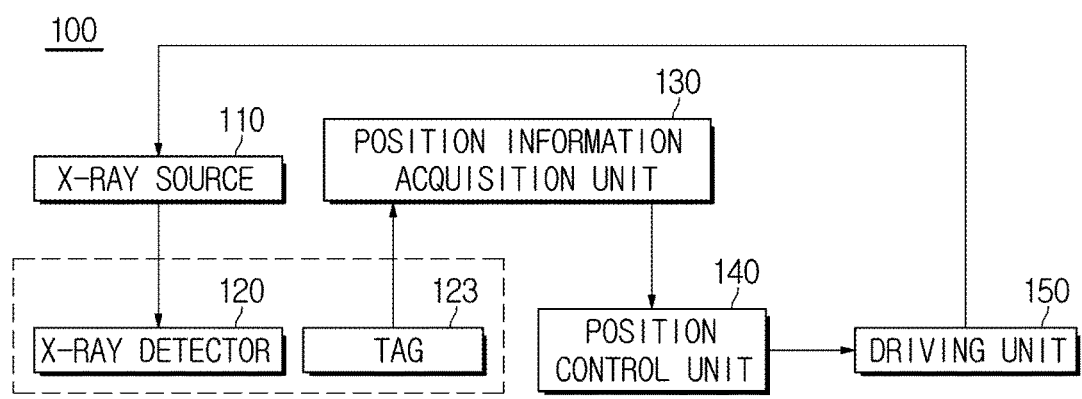
FIG. 2 is a block diagram illustrating a mobile X-ray imaging apparatus according to an exemplary embodiment.

FIG. 2 is a block diagram illustrating a mobile X-ray imaging apparatus 100 according to an exemplary embodiment.

Referring to FIG. 2, the mobile X-ray imaging apparatus 100 according to an exemplary embodiment includes an X-ray source 110 to generate X-rays and to irradiate an object with the generated X-rays, an X-ray detector 120 to detect X-rays having passed through the object, a position information acquisition unit 130 (e.g., position information acquirer) to acquire position information of the X-ray source 110 relative to the X-ray detector 120, a position control unit 140 (e.g., position controller) to control the X-ray source 110 to move to a position corresponding to the X-ray detector 120 from a certain position in 3D space, based on the acquired relative position information, and a driving unit 150 (e.g., driving mechanism) to move the X-ray source 110 according to a control signal of the position control unit 140.

The mobile X-ray imaging apparatus 100 may perform projection radiography to generate a 2D image or perform tomosynthesis or stereo radiography to generate a 3D or stereoscopic image.

According to an exemplary embodiment, the X-ray detector 120 is configured as a portable X-ray detector. The portable X-ray detector may be implemented as a wireless X-ray detector, or may be connected via a data cable or a power cable according to a data transmission method or a power supply method.

The mobile X-ray imaging apparatus 100 may minimize movement of the object and, as illustrated in FIG. 1B, the X-ray detector 120 may be fixed at a position corresponding to a site of the object to be X-ray imaged and the X-ray source 110 may be aligned with the position of the X-ray detector 120.

The position information acquisition unit 130 acquires position information of the X-ray source 110 relative to the X-ray detector 120 by sensing the position of the X-ray detector 120 and aligns the X-ray source 110 with the position of the X-ray detector 120 using the relative position information. For this operation, tags 123 may be installed on the X-ray detector 120 so that the position of the X-ray detector 120 can be sensed. A detailed description of the tags 123 will be described below.

Figure 3:
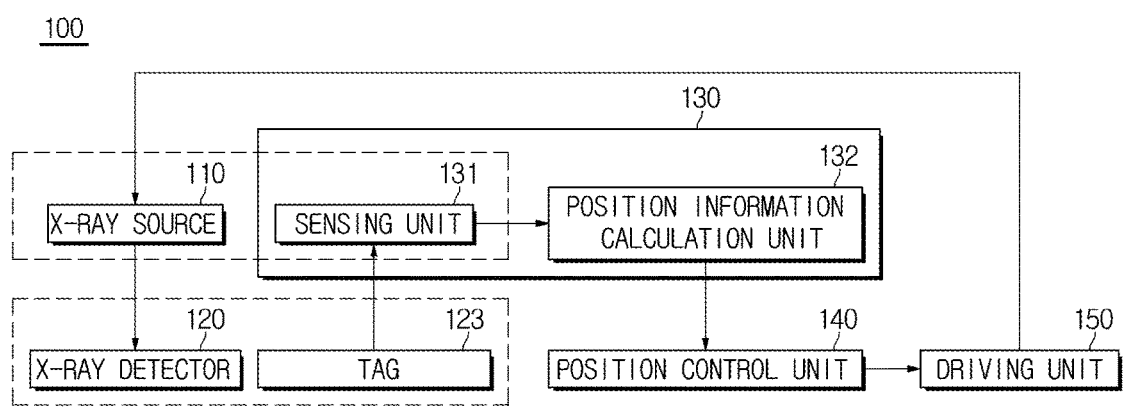
FIG. 3 is a control block diagram illustrating the configuration of a position information acquisition unit of the mobile X-ray imaging apparatus according to an exemplary embodiment.

FIG. 3 is a control block diagram illustrating the configuration of the position information acquisition unit 130 of the mobile X-ray imaging apparatus 100 according to an exemplary embodiment.

Referring to FIG. 3, the position information acquisition unit 130 includes a sensing unit 131 (e.g., sensor) to sense the position of the X-ray detector 120 and a position information calculation unit 132 (e.g., position information calculator) to calculate position information of the X-ray source 110 relative to the X-ray detector 120 based on an output signal of the sensing unit 131. The tags 123 are installed on the X-ray detector 120, and the operation of sensing the position of the X-ray detector 120 by the sensing unit 131 includes sensing the tags 123 installed on the X-ray detector 120.

The sensing unit 131 and the position information calculation unit 132 may be configured as a single physical module or as separate physical modules such that the sensing unit 131 is located at a position that enables sensing of the X-ray detector 120 and the position information calculation unit 132 is included in a control unit to control the mobile X-ray imaging apparatus 100.

According to an exemplary embodiment, the sensing unit 131 may be installed at the X-ray source 110. When the sensing unit 131 is installed at the X-ray source 110, there is no need to sense the position of the X-ray source 110 and the relative position information of the X-ray source 110 to the X-ray detector 120 may be acquired using position sensing results of the X-ray detector 120 alone.

However, exemplary embodiments are not limited to the above examples. In another exemplary embodiment, tags 123 may be installed at the X-ray source 110 and the sensing unit 131 may be located at a third position which is not at the position where the X-ray source 110 or the X-ray detector 120 is located, to sense the position of each of the X-ray source 110 and the X-ray detector 120. According to another exemplary embodiment, the sensing unit 131 may be installed at the X-ray detector 120 and the tags 123 may be installed at the X-ray source 110, or the sensing unit 131 may be installed at each of the X-ray source 110 and the X-ray detector 120 and sense the tags 123 present at a third position. An exemplary embodiment of each case will now be described with reference to the following drawings.

According to an exemplary embodiment, the third position where the tags 123 or the sensing unit 131 may be located may be a certain position in a certain space including one of the X-ray source 110 and the X-ray detector 120, for example, a main body. The third position is not, however, limited to this configuration and may be a position enabling the tags 123 installed at the X-ray source 110 and the X-ray detector 120 to be sensed or a position enabling sensing by the sensing unit 131 installed at the X-ray source 110 and the X-ray detector 120.

Figure 4:
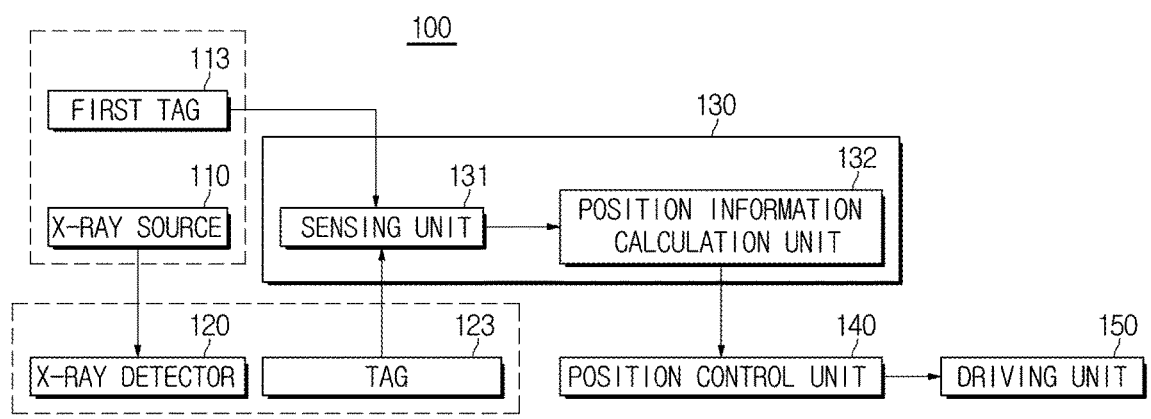
FIG. 4 is a control block diagram illustrating a case in which the position of an X-ray source of the mobile X-ray imaging apparatus according to an exemplary embodiment is separately sensed.

FIG. 4 is a control block diagram illustrating a case in which the position of the X-ray source 110 of the mobile X-ray imaging apparatus 100 according to an exemplary embodiment is separately sensed.

Referring to FIG. 4, when the positions of the X-ray source 110 and the X-ray detector 120 are separately sensed, a first tag 113 enabling the position of the X-ray source 110 to be sensed may be installed at the X-ray source 110, and a second tag 123 enabling the position of the X-ray detector 120 to be sensed may be installed at the X-ray detector 120.

The sensing unit 131 of the position information acquisition unit 130 senses the position of the X-ray source 110 by sensing the first tag 113 and senses the position of the X-ray detector 120 by sensing the second tag 123.

The sensing unit 131 may be installed on a main body of the mobile X-ray imaging apparatus 100 or located at a certain position in a certain space including the X-ray detector 120 and the X-ray source 110. As described above, the position of the sensing unit 131 is not particularly limited so long as the sensing unit 131 is located at a position enabling the X-ray detector 120 and the X-ray source 110 to be sensed.

The position information calculation unit 132 calculates position information of the X-ray source 110 relative to the X-ray detector 120 based on output values of the sensing unit 131, and the position control unit 140 controls the X-ray source 110 to move to a position corresponding to the X-ray detector 120 based on the calculated relative position information.

The mobile X-ray imaging apparatus 100 according to exemplary embodiments may include both the case illustrated in FIG. 3 and the case illustrated in FIG. 4. In the following exemplary embodiments, however, only the case in which the sensing unit 131 is installed at the X-ray source 110 as illustrated in FIG. 3 will be described by way of example for convenience of explanation.

FIGS. 5, 6, 7, 8 and 9 are exterior views of the mobile X-ray imaging apparatus 100 according to an exemplary embodiment.

Hereinafter, the operation by which the mobile X-ray imaging apparatus 100 acquires the position information of the X-ray source 110 relative to the X-ray detector 120 will be described in detail with reference to the control block diagram of FIG. 3 together with FIGS. 5 to 9.

Figure 5:
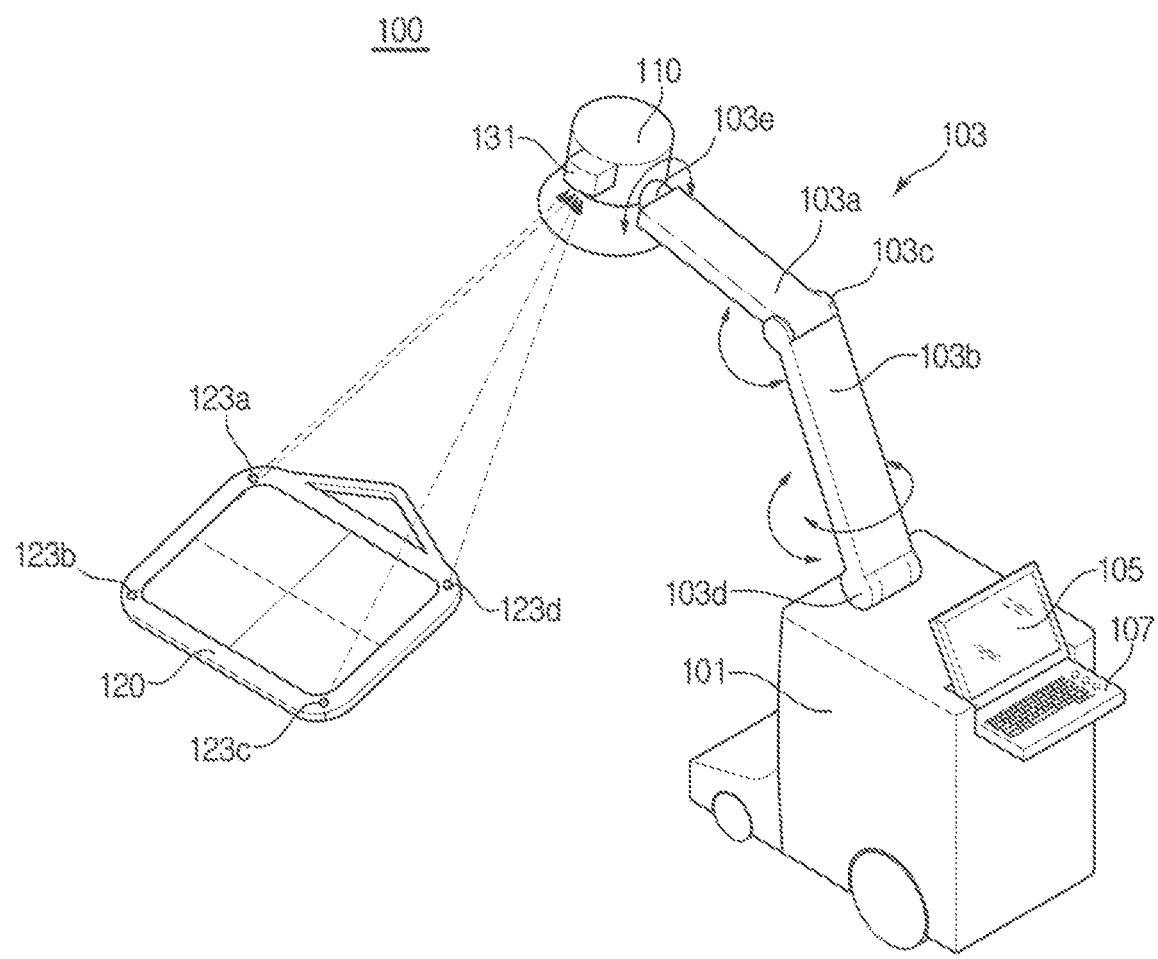
FIGS. 5, 6, 7, 8 and 9 are exterior views of the mobile X-ray imaging apparatus according to an exemplary embodiment.

Referring to FIG. 5, the mobile X-ray imaging apparatus 100 includes a support arm 103 installed at a main body 101, which is movable, and the support arm 103 is provided at an end thereof with a source connection unit 103e at which the X-ray source 110 is installed. The support arm 103 is rotatable about a mounting unit 103d in a direction parallel to the ground.

The support arm 103 includes a first support arm 103a at which the X-ray source 110 is installed and a second support arm 103b installed at the main body 101. The first support arm 103a and the second support arm 103b may be coupled to each other via an arm connection unit 103c, and tilt angles thereof may be respectively adjusted based on the arm connection unit 103c and the mounting unit 103d. Accordingly, the X-ray source 110 may freely move in 3D space.

However, the exemplary embodiment illustrated in FIG. 5 is only an example of an exterior appearance of the mobile X-ray imaging apparatus 100. That is, the support arm 103 may be configured in many other ways, for example, as a single element or may further include additional sub-support arms similar to the first support arm 103a and the second support arm 103b.

Although not shown in FIG. 5, when X-ray imaging is performed and the X-ray detector 120 detects X-rays and converts the X-rays into electrical signals, a control unit of the mobile X-ray imaging apparatus 100 performs image processing to generate an X-ray image of an object. The X-ray image may be displayed through a display unit 105 included on the main body 101, and a user may input control commands for overall operations of the mobile X-ray imaging apparatus 100 via an input unit 107.

As described above with reference to FIG. 3, the tags 123 may be installed at the X-ray detector 120. According to an exemplary embodiment, the tags 123 may include a first tag 123a, a second tag 123b, a third tag 123c, and a fourth tag 123d that are respectively installed at four corners of the X-ray detector 120. An outer side of the X-ray detector 120 is surrounded by a housing, and a detection module to detect X-rays is provided inside of the housing. Each of the first tag 123a, the second tag 123b, the third tag 123c, and the fourth tag 123d may be installed at an outer side of the detection module on the housing so as not to affect detection of X-rays.

A grid is provided at an inner or outer side of the housing of the X-ray detector 120 to absorb scattered X-rays, and the tags 123 may also be installed at the grid.

The sensing unit 131 is installed at the X-ray source 110 and senses the tags 123 installed at the X-ray detector 120.

The relative position information of the X-ray source 110 to the X-ray detector 120 includes position information and relative angle information therebetween. According to the present exemplary embodiment, the position information is relative between the X-ray source 110 and the X-ray detector 120, and thus, the position information of the X-ray detector 120 relative to the X-ray source 110 or the position information of the X-ray source 110 relative to the X-ray detector 120 may be interpreted to have the same meaning. In this regard, relative angles refer to tilting degrees of the X-ray detector 120 with respect to the X-ray source 110.

Unlike a general X-ray imaging apparatus, in the mobile X-ray imaging apparatus 100, the X-ray source 110 and the X-ray detector 120 may freely move to various positions, and thus a distance and angle therebetween may also have various magnitudes and directions.

As illustrated in FIG. 5, when the tags 123 are respectively installed at the four corners of the X-ray detector 120, the sensing unit 131 may sense each tag 123, and the position information calculation unit 132 may estimate distances between the X-ray source 110 and each corner of the X-ray detector 120 from output signals of the sensing unit 131. In addition, a distance and relative angle information between the X-ray source 110 and the X-ray detector 120 may be calculated using the position relationship between the four tags 123 and the distances between the X-ray source 110 and each corner of the X-ray detector 120.

However, exemplary embodiments of the mobile X-ray imaging apparatus 100 are not limited to the above examples. In other words, the tags 123 may be installed only at two corners or three corners of the X-ray detector 120, and the positions or number of the tags 123 may vary according to a calculation method of calculating position information.

Figure 6:
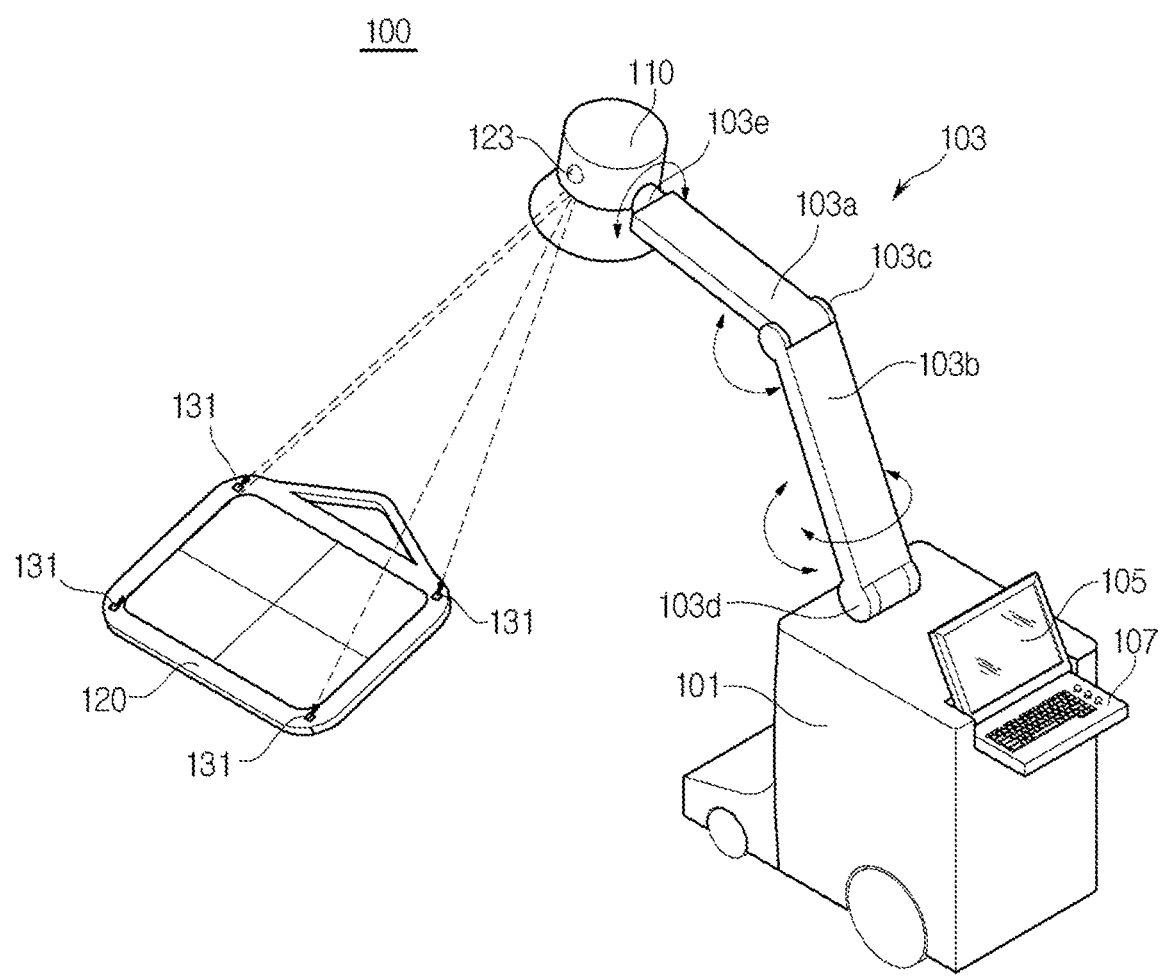

In addition, as illustrated in FIG. 6, the sensing units 131 may be installed at the X-ray detector 120, and the tag 123 may be installed at the X-ray source 110. When the sensing units 131 are installed at the X-ray detector 120, the sensing units 131 may be respectively installed at two, three or four corners of the X-ray detector 120, the tag 123 installed at the X-ray source 110 may be sensed from the position of each corner, and the position information calculation unit 132 may calculate relative position information between the X-ray detector 120 and the X-ray source 110 from the output signals of the sensing units 131.

Figure 7:
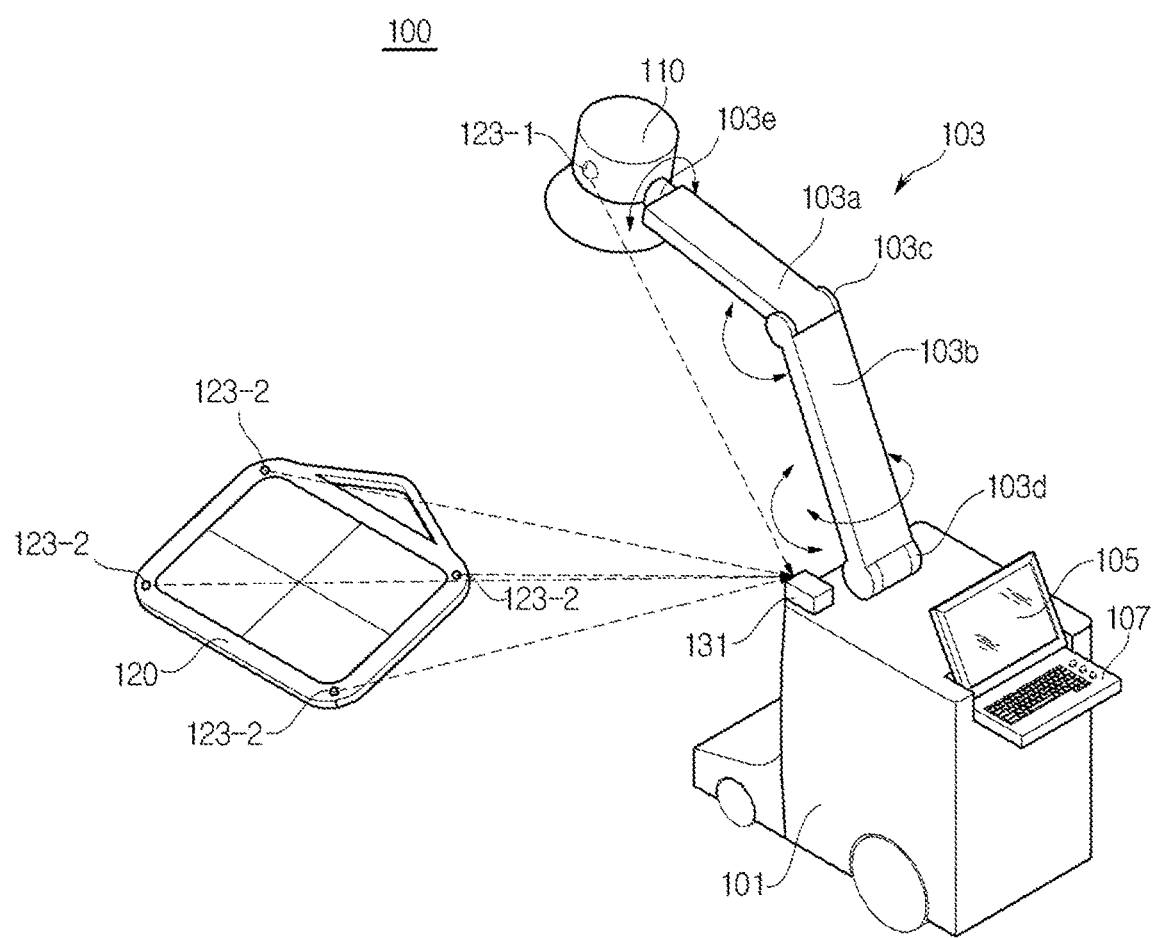

In addition, as illustrated in FIG. 7, a tag 123-1 and a tag 123-2 may be installed at the X-ray source 110 and the X-ray detector 120, respectively, and the sensing unit 131 may be located at an arbitrary position in a certain space including the X-ray detector 120 and the X-ray source 110 to sense each of the tags 123a and 123b. According to an exemplary embodiment, the sensing unit 131 may be installed at the main body 101. In this case, the tags 123-2 installed at the X-ray detector 120 may be respectively installed at two, three or four corners of the X-ray detector 120. When the sensing unit 131 senses the tag 123-1 installed at the X-ray source 110 and the tags 123-2 installed at the X-ray detector 120, the position information calculation unit 132 may calculate distances between the sensing unit 131 and each of the tags 123-1 and 123-2 from the output signals of the sensing unit 131 and calculate relative position information between the X-ray source 110 and the X-ray detector 120 using the calculated distances.

Figure 8:
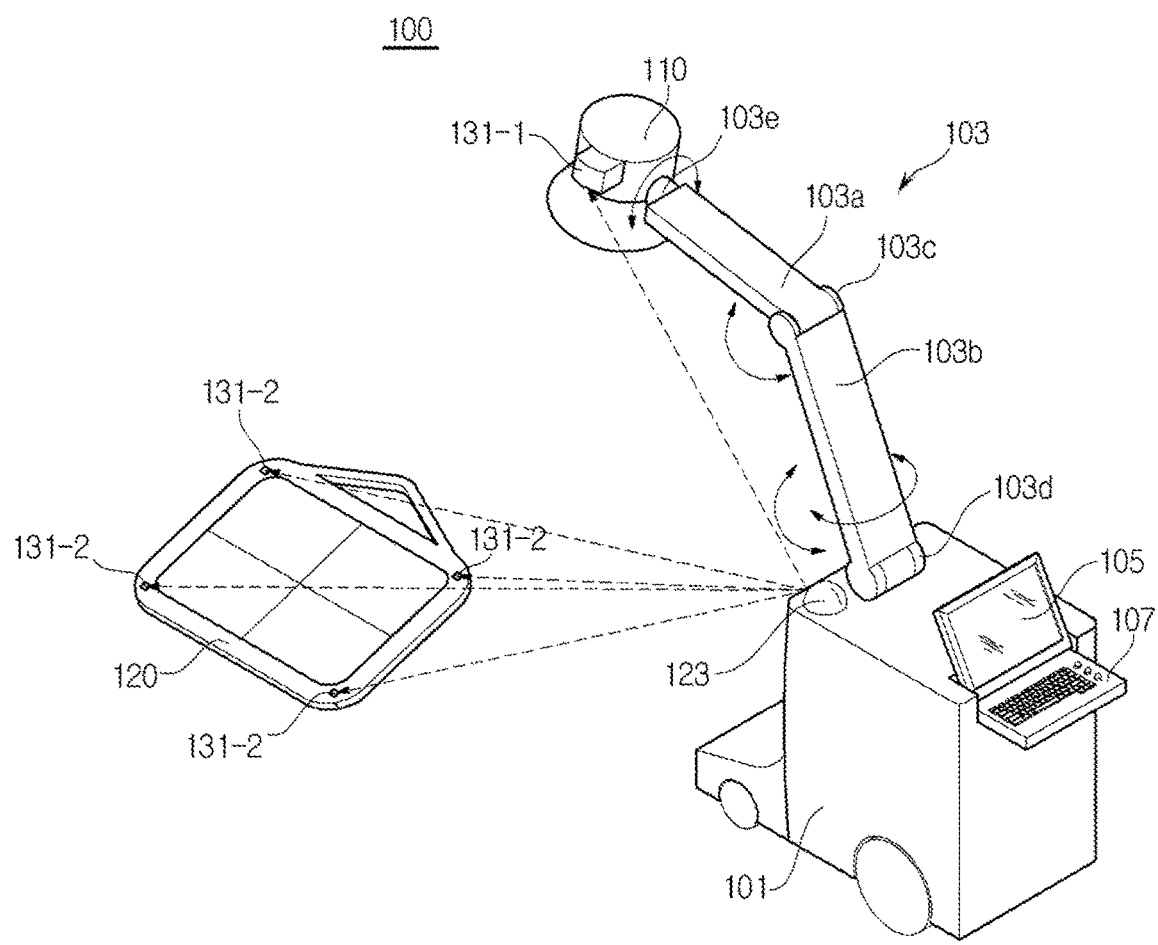

In addition, as illustrated in FIG. 8, a sensing unit 131-1 and sensing units 131-2 may be installed at the X-ray source 110 and the X-ray detector 120, respectively, and each of the sensing units 131-1 and 131-2 may sense the tag 123 located at an arbitrary position in a certain space including the X-ray detector 120 and the X-ray source 110. According to an exemplary embodiment, the tag 123 may be installed at the main body 101. In this case, the sensing units 131-2 installed at the X-ray detector 120 may be respectively installed at two, three or four corners of the X-ray detector 120. When each of the sensing units 131-1 and 131-2 senses the tag 123 and transmits an output signal to the position information calculation unit 132, the position information calculation unit 132 may calculate relative position information of the X-ray detector 120 and the X-ray source 110 from the output signal of each of the sensing units 131-1 and 131-2.

Sensing the position of the X-ray detector 120 by the sensing unit 131 via the tag 123, e.g., sensing the tag 123 by the sensing unit 131, may be performed using various methods.

In particular, the tag 123 and the sensing unit 131 may be each independently implemented as a passive type or an active type. In this regard, the passive type refers to a configuration in which signals are not output, and the active type refers to a configuration in which signals are output. Thus, the tag 123 may generate a signal and the sensing unit 131 may sense the signal, or the tag 123 may not generate a signal and the sensing unit 131 may output a signal such as visible light, infrared light, ultrasonic waves, or the like and sense an echo signal reflected from the tag 123. In this regard, types of signals output from the sensing unit 131 are not limited, and any signal that returns after being reflected by the tag 123, a magnitude of which varies according to a distance between the tag 123 and the sensing unit 131, may be used. For example, when the tag 123 generates a wireless signal such as a radio frequency (RF) signal, an infrared light signal, or the like, the sensing unit 131 senses the signal and outputs the signal to the position information calculation unit 132. The magnitude or phase of the signal sensed according to the distance between the tag 123 and the sensing unit 131 varies, and thus, the position information calculation unit 132 may estimate a distance between the tag 123 and the X-ray source 110 from changes in magnitude or phase of the output signal of the sensing unit 131.

To increase accuracy of the relative position information to be calculated, signals from multiple tags 123, e.g., three or four tags 123 may be generated at time intervals. In addition, several signals may be generated from a single tag at time intervals.

According to another exemplary embodiment, when the tag 123 generates a magnetic signal, the sensing unit 131 senses the magnetic signal and outputs the signal to the position information calculation unit 132. For this operation, the tag 123 may be a magnetic field generator or may be configured using a magnetic material, and the sensing unit 131 may be a magnetic sensor.

In this case, changes in a magnetic field at the sensing unit 131 may vary according to the distance between the sensing unit 131 and the tag 123 and the magnitude or shape of the output signal may vary. Thus, the position information calculation unit 132 may estimate the distance between the tag 123 and the X-ray source 110 from changes in magnitude or shape of the signal output from the sensing unit 131.

Figure 9:
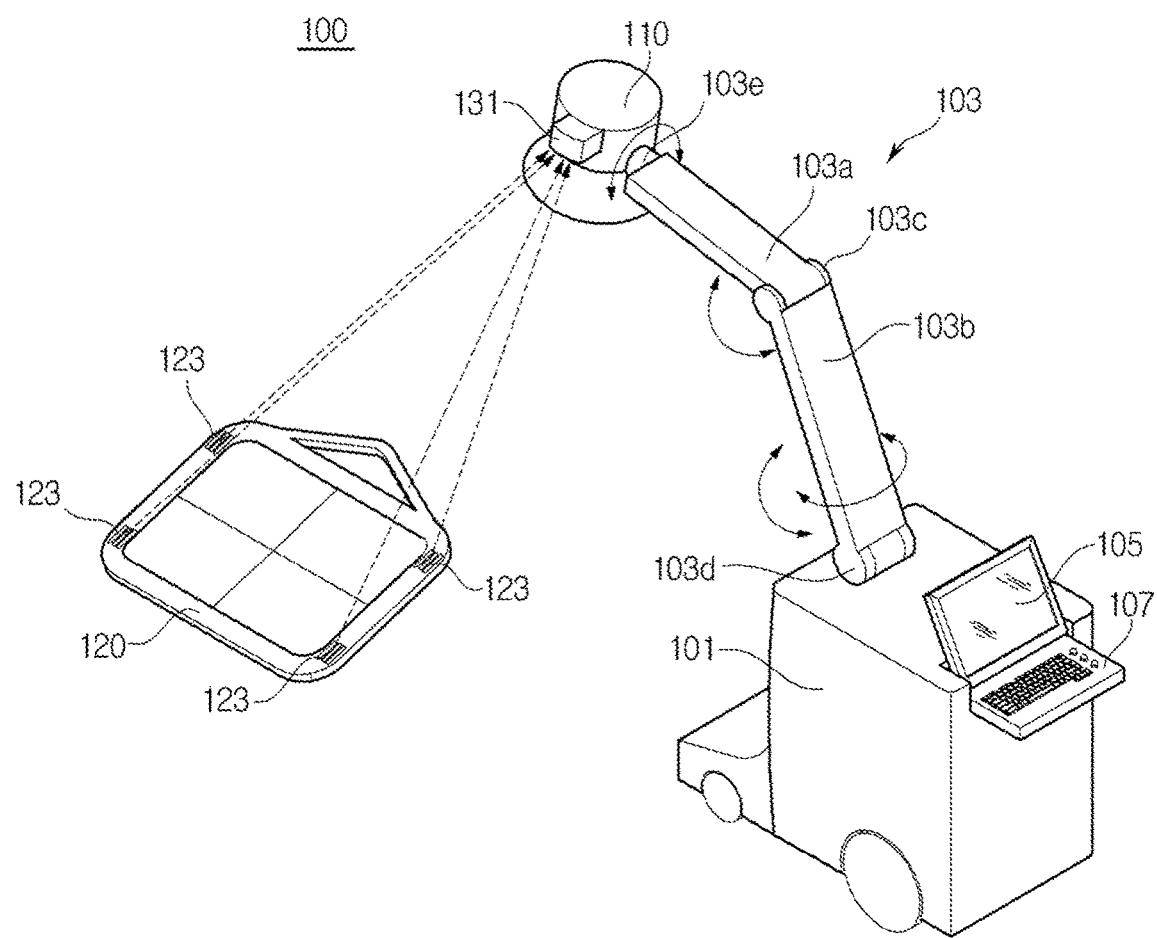

According to another exemplary embodiment, as illustrated in FIG. 9, the tags 123 may be embodied in a predetermined optical pattern, and the sensing unit 131 may be embodied as an image sensor to sense the tags 123.

Figure 10:
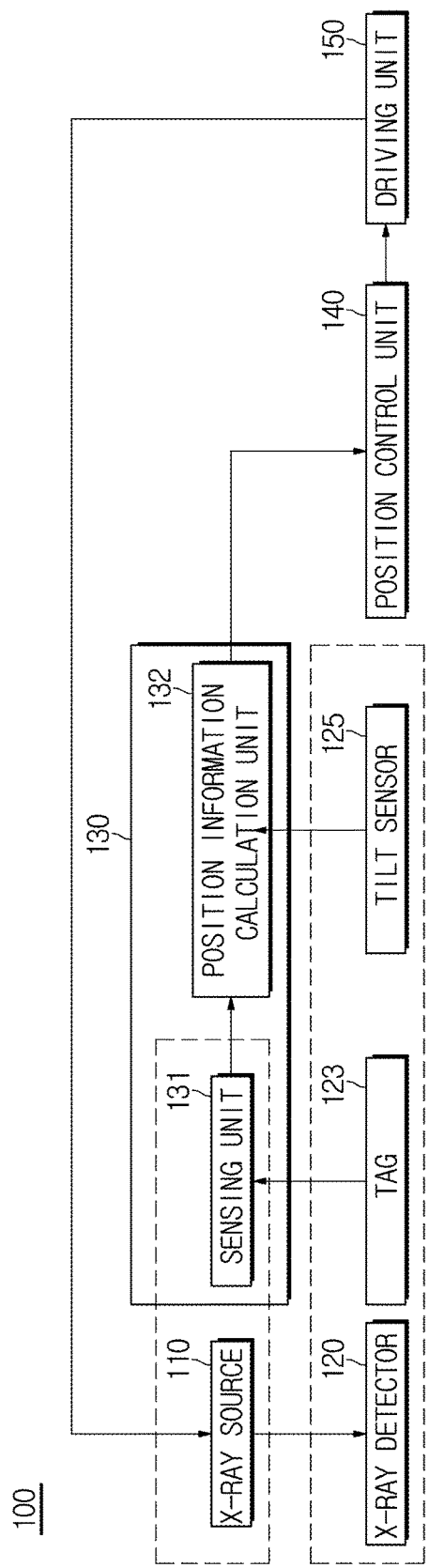
FIG. 10 is a control block diagram illustrating the acquisition of angle information between the X-ray source and an X-ray detector, according to another exemplary embodiment.

However, the above-described examples of the mobile X-ray imaging apparatus 100 are provided for illustrative purposes only, and exemplary embodiments of the mobile X-ray imaging apparatus 100 are not limited in terms of the method of sensing the tags 123 by the sensing unit 131. FIG. 10 is a control block diagram illustrating an acquisition of angle information between the X-ray source 110 and the X-ray detector 120, according to another exemplary embodiment.

Referring to FIG. 10, the X-ray detector 120 may further include a tilt sensor 125 to sense the tilt of the X-ray detector 120.

When tilt information of the X-ray detector 120 is identified, it is easier for the position information calculation unit 132 to calculate the position information of the X-ray source 110 relative to the X-ray detector 120. Thus, the position information calculation unit 132 may calculate distance information and angle information of the X-ray source 110 and the X-ray detector 120 from an output signal of the sensing unit 131 that has sensed the tags 123 and an output signal of the tilt sensor 125.

When the distance and angle information are calculated from the output signal of the sensing unit 131, it is advantageous in that no separate element is needed other than the tag 123 and the sensing unit 131. When the X-ray detector 120 includes the tilt sensor 125, it is advantageous in that a computational load of the position information calculation unit 132 is reduced.

Referring back to FIG. 3, when the position information calculation unit 132 calculates a distance between the X-ray source 110 and the X-ray detector 120 and an angle of the X-ray source 110 relative to the X-ray detector 120, the position control unit 140 calculates a control amount for moving the X-ray source 110 to a position corresponding to the X-ray detector 120, based thereon. The position of the X-ray source 110, corresponding to the X-ray detector 120, may be pre-stored as a certain value and applied as a default, or may be separately set according to several variables as described below.

The position control unit 140 transmits a control signal corresponding to the calculated control amount to the driving unit 150. The driving unit 150 includes a motor and a drive. The drive generates a motor driving signal and transmits the motor driving signal to the motor and the motor generates power according to the driving signal to move the support arm 103.

Referring back to FIG. 5, the driving unit 150 may be included in each of the arm connection unit 103c and the mounting unit 103d, and the position control unit 140 may control a rotation angle and tilt angle of the support arm 103 via the driving unit 150.

In addition, the driving unit 150 may move the main body 101 as desired. In this case, the driving unit 150 may include a motor to drive movement of the main body 101 and a drive, and the position control unit 140 may calculate a control amount and transmit a control signal to the driving unit 150 of the main body 101.

Figure 11:
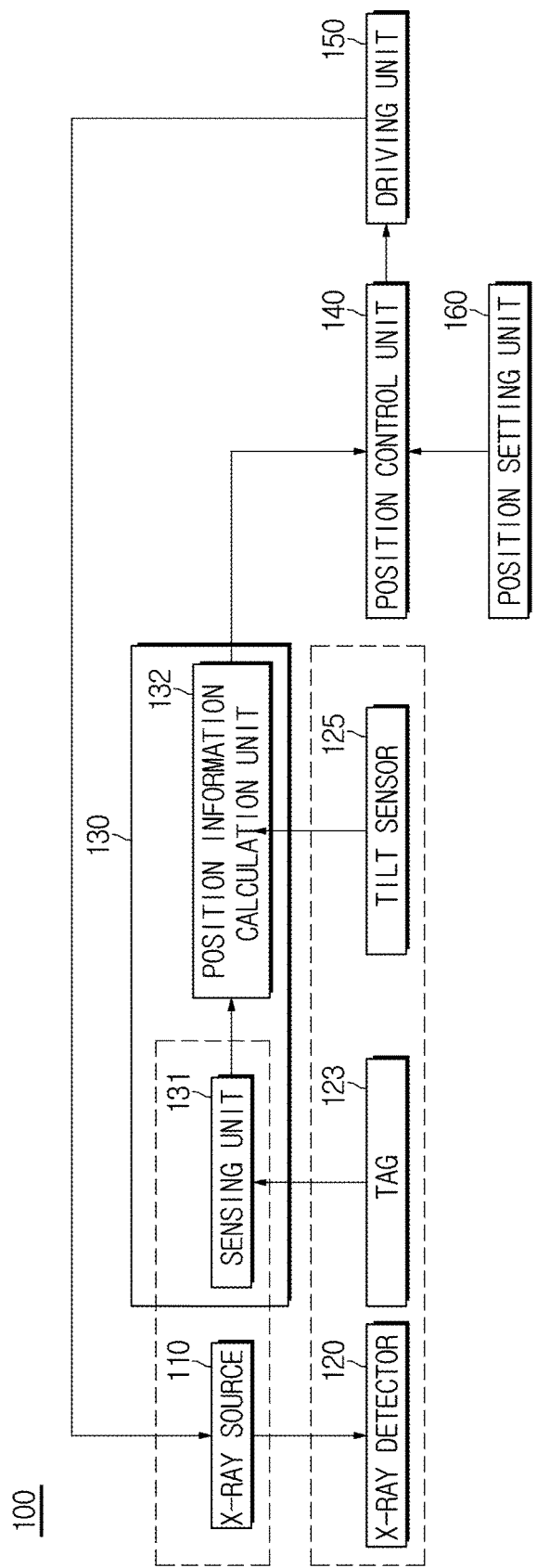
FIG. 11 is a control block diagram illustrating a mobile X-ray imaging apparatus capable of setting a target position of the X-ray source relative to the X-ray detector according to an exemplary embodiment.

FIG. 11 is a control block diagram illustrating the mobile X-ray imaging apparatus 100 capable of setting a target position of the X-ray source 110 relative to the X-ray detector 120 according to an exemplary embodiment.

As described above, the position control unit 140 calculates the control amount for moving the X-ray source 110 to the position corresponding to the X-ray detector 120. For this operation, the mobile X-ray imaging apparatus 100 may further include a position setting unit 160 (e.g., position setter) to set the position of the X-ray source 110 which corresponds to a position of the X-ray detector 120, i.e., to set a target position of the X-ray source 110. In this regard, the target position is a relative position based on the X-ray detector 120 and may be defined by a distance between the X-ray source 110 and the X-ray detector 120 and an angle of the X-ray source 110 relative to the X-ray detector 120.

An optimum distance between the X-ray source 110 and the X-ray detector 120 and an angle of the X-ray source 110 relative to the X-ray detector 120 may vary according to a site of an object to be X-ray imaged, conditions of the object, application of X-ray images, or the like. Thus, algorithms for setting the target position of the X-ray source 110 according to several variables may be pre-stored in the position setting unit 160 and, when information corresponding to the variables is input thereto, the position setting unit 160 may set the target position of the X-ray source 110 according to the pre-stored algorithms. The information corresponding to the variables may be input from the system itself or input by a user via the input unit 107 included in the main body 101.

The position control unit 140 receives current position information of the X-ray source 110 relative to the X-ray detector 120 from the position information calculation unit 132, receives the target position information of the X-ray source 110 from the position setting unit 160, and calculates a control amount for moving the X-ray source 110 to a target position from the current position.

In addition, the position control unit 140 may control the position of the X-ray source 110 relative to the X-ray detector 120 and also control a tilt angle of the X-ray source 110. Referring back to FIG. 5, a tilt angle sensor may be installed at the source connection unit 103e to sense a current tilt angle of the X-ray source 110 and to control the tilt angle of the X-ray source 110 according to target position information of the X-ray source 110.

For this operation, the driving unit 150 may also be included in the source connection unit 103e, and the position control unit 140 may calculate a required control amount and transmit a control signal corresponding thereto to the driving unit 150 included in the source connection unit 103e.

Figure 12:
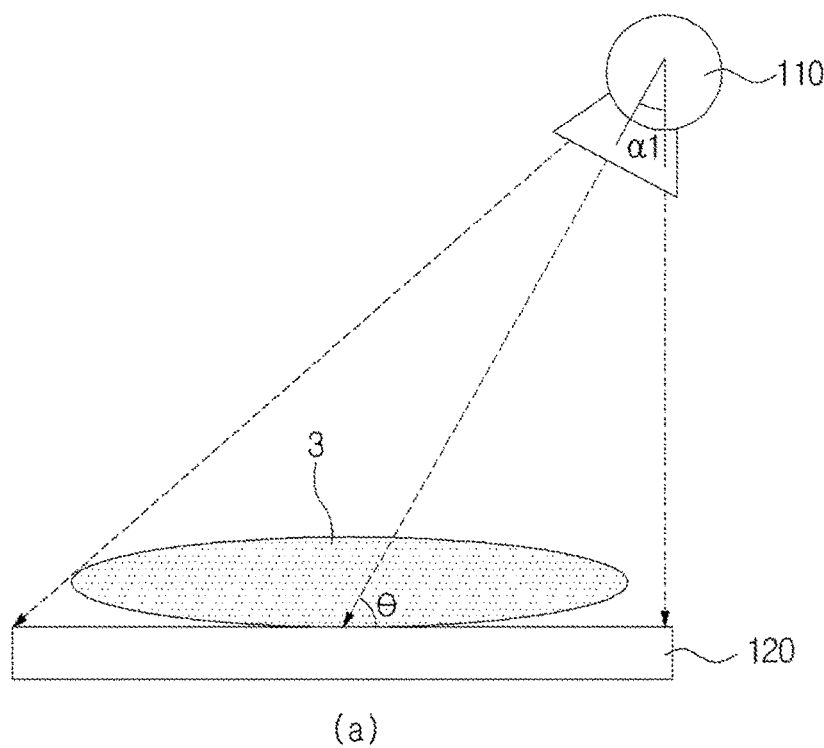
FIG. 12 is a schematic view illustrating the control of a tilt angle of the X-ray source according to an exemplary embodiment.
Figure 12:
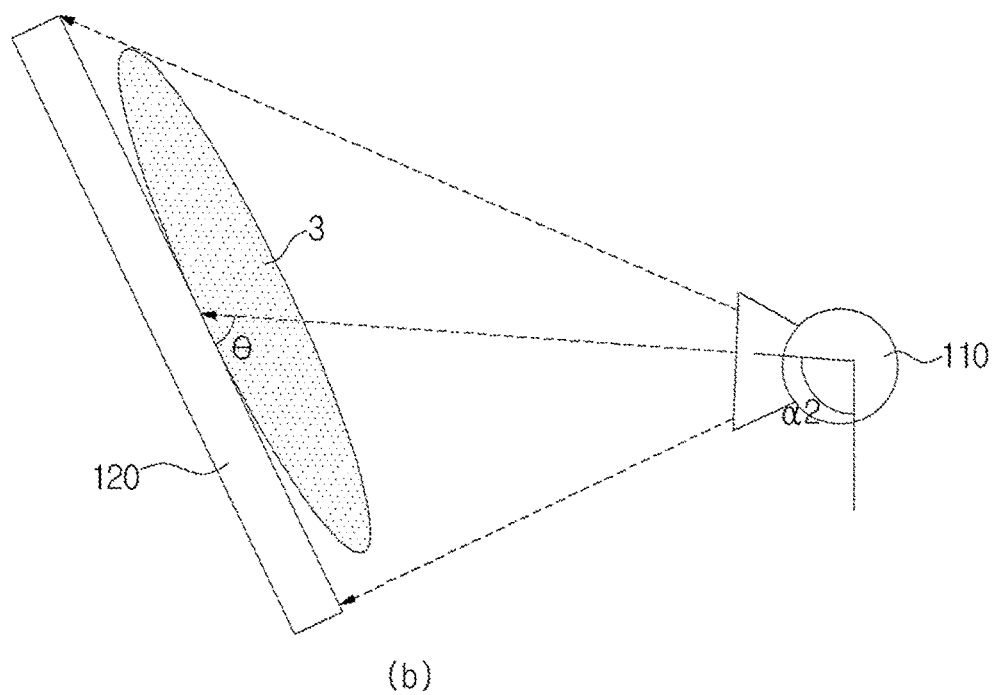

FIG. 12 is a schematic view illustrating control of the tilt angle of the X-ray source 110 according to an exemplary embodiment.

X-rays may be vertically incident or incident at an angle on the X-ray detector 120 according to a site of an object to be X-ray imaged, conditions of the object, application of X-ray images, or the like. An incident angle of X-rays may vary according to the angle of the X-ray source 110 relative to the X-ray detector 120 and the tilt angle of the X-ray source 110. In this regard, the tilt angle of the X-ray source 110 indicates an inclination angle of the X-ray source 110 based on a vertical line with respect to the ground.

As illustrated in FIG. 12, when the position setting unit 160 sets an angle of θ as a target incident angle, an angle of the X-ray source 110 relative to the X-ray detector 120 is set to θ, assuming that the X-ray detector 120 lies parallel to the ground, and the X-ray source 110 is tilted by an angle of α1. However, when the X-ray detector 120 is tilted by a certain angle with respect to the ground, the X-ray source 110 has to be tilted by an angle of α2 so that the incident angle is θ.

As illustrated in FIG. 10, when the tilt sensor 125 is installed at the X-ray detector 120 and a tilt with respect to the ground is identified, the position control unit 140 may determine the target tilt angle, calculate a control amount for the tilt angle, and automatically control the tilt angle of the X-ray source 110.

According to another exemplary embodiment, when the sensing units 131 or the tags 123 are installed at opposite ends of an inlet of the X-ray source 110, the position control unit 140 may determine the target tilt angle of the X-ray source 110 by analyzing output signals of the sensing units 131, calculate a control amount therefor, and automatically control the tilt angle of the X-ray source 110.

However, exemplary embodiments of the mobile X-ray imaging apparatus 100 are not limited to the above examples, and the tilt angle of the X-ray source 110 may be controlled in other ways, for example, manually controlled by a user.

Figure 13:
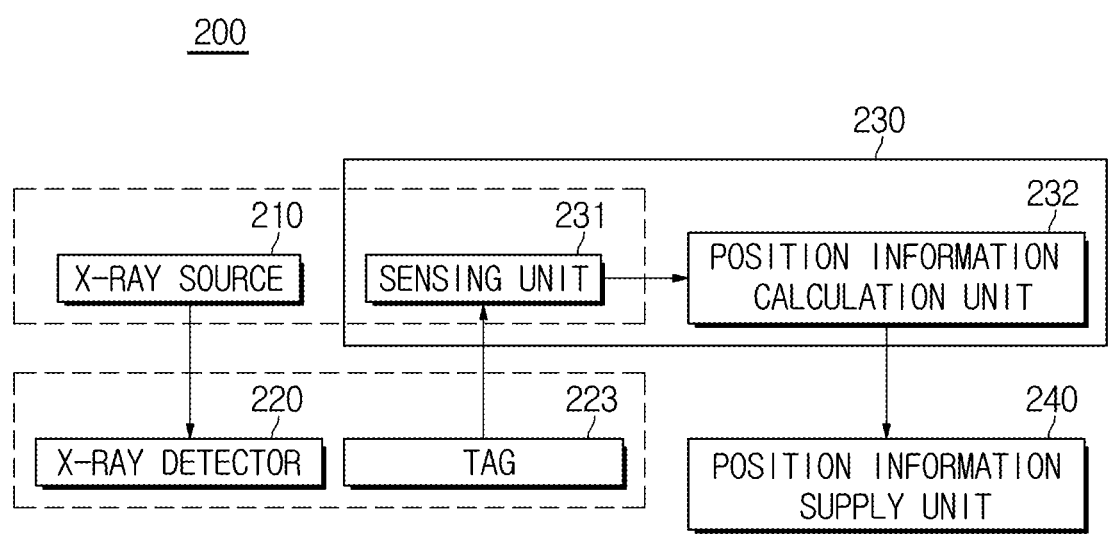
FIG. 13 is a control block diagram illustrating a mobile X-ray imaging apparatus according to another exemplary embodiment.

FIG. 13 is a control block diagram illustrating a mobile X-ray imaging apparatus 200 according to another exemplary embodiment.

Referring to FIG. 13, the mobile X-ray imaging apparatus 200 according to another exemplary embodiment includes an X-ray source 210 to generate X-rays and irradiate an object with the generated X-rays, an X-ray detector 220 to detect X-rays having passed through the object, a position information acquisition unit 230 to acquire position information of the X-ray source 210 relative to the X-ray detector 220, and a position information supply unit 240 (e.g., position information supplier) to supply the acquired position information to a user.

The X-ray source 210, the X-ray detector 220, and the position information acquisition unit 230 may be implemented the same as those of the mobile X-ray imaging apparatus 100 according to the previously described exemplary embodiments, and thus, a detailed description thereof will be omitted here. Thus, in the mobile X-ray imaging apparatus 200 according to the present exemplary embodiment, a sensing unit 231 may also sense a position of each of the X-ray source 210 and the X-ray detector 220 from a third position, or the sensing unit 231 may be installed at the X-ray detector 220 and a tag 223 may be installed at the X-ray source 210. Alternatively, the sensing unit 231 may be installed at each of the X-ray source 210 and the X-ray detector 220 to sense the tag 223 at the third position. In the following discussion of the exemplary embodiment, a case in which the sensing unit 231 is installed at the X-ray source 210 to sense the tag 223 installed at the X-ray detector 220 will be described by way of example.

The position information supply unit 240 may provide various kinds of position information of the X-ray source 210 relative to the X-ray detector 220. In this regard, the position information supply unit 240 may provide quantitative information itself or information which is processed so as for a user to easily identify the information. In addition, the information may be visually or audibly provided.

When the position information of the X-ray source 210 relative to the X-ray detector 220 is provided via the position information supply unit 240, a user may identify the relative position relationship between the X-ray source 210 and the X-ray detector 220 and manually move the X-ray source 210 to a position corresponding to the X-ray detector 220.

Figure 14:
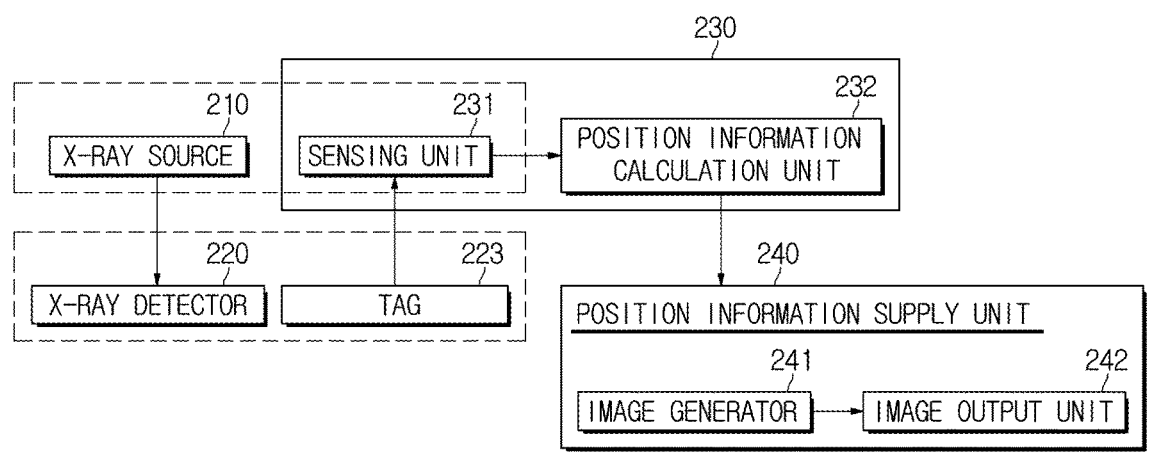
FIG. 14 is a control block diagram of the mobile X-ray imaging apparatus that visually provides position information of an X-ray source relative to an X-ray detector through processing.

FIG. 14 is a control block diagram of the mobile X-ray imaging apparatus 200 that visually provides the position information of the X-ray source 210 relative to the X-ray detector 220 through processing.

Referring to FIG. 14, the position information supply unit 240 includes an image generator 241 to generate a position information image including the position information of the X-ray source 210 relative to the X-ray detector 220 and an image output unit 242 (e.g., image outputter) to output the generated position information image.

The image generator 241 may generate various types of position information images including the position information of the X-ray source 210 relative to the X-ray detector 220. For example, the position information of the X-ray source 210 relative to the X-ray detector 220 may be represented as coordinates in 3D space, or as an avatar or icon to intuitively show the X-ray source 210 and the X-ray detector 220. It is understood that the image generator 241 may generate many different types of images representing position information, and is not limited to any particular type.

In addition, the position information image may further include information regarding the target position of the X-ray source 210. The target position of the X-ray source 210 may be stored as a default or set in consideration of various variables.

Figure 15:
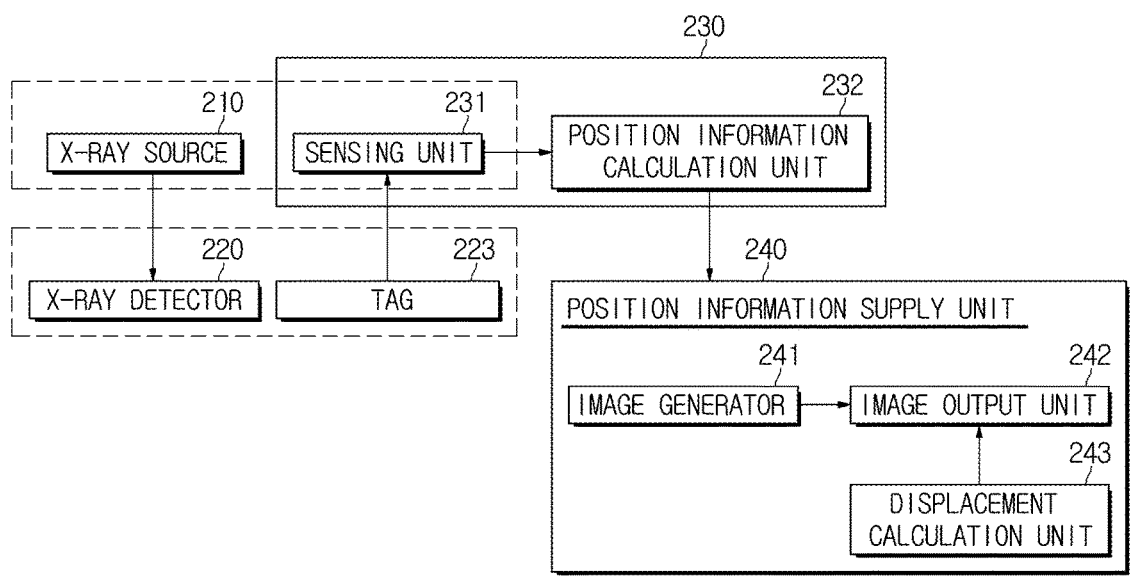
FIGS. 15 and 16 are control block diagrams illustrating the mobile X-ray imaging apparatus that further provides information regarding a displacement of the X-ray source.
Figure 16:
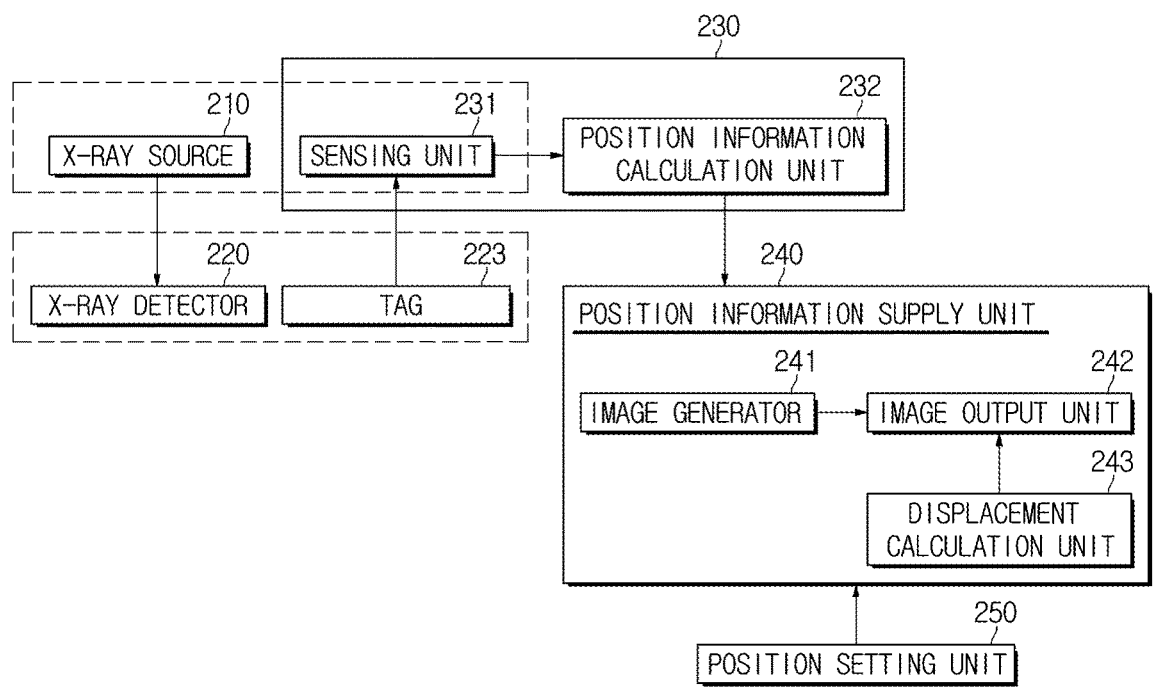

FIGS. 15 and 16 are control block diagrams illustrating the mobile X-ray imaging apparatus 200 that further provides information regarding a displacement of the X-ray source 210.

Referring to FIG. 15, the position information supply unit 240 may further include a displacement calculation unit 243 (e.g., displacement calculator) to calculate the displacement of the X-ray source 210. The displacement calculation unit 243 calculates a displacement and moving direction for moving the X-ray source 210 to a target position from the current position using the position information of the X-ray source 210 relative to the X-ray detector 220 and the target position of the X-ray source 210.

The image generator 241 may generate a position information image including information regarding the target position and displacement of the X-ray source 210 as well as the position information of the X-ray source 210 relative to the X-ray detector 220 and display the generated position information image via the image output unit 242.

In addition, as illustrated in FIG. 16, the mobile X-ray imaging apparatus 200 may further include a position setting unit 250 to set the target position of the X-ray source 210 according to various variables, and the displacement calculation unit 243 may calculate the displacement and moving direction of the X-ray source 210 in consideration of the target position set by the position setting unit 250.

Figure 17A:
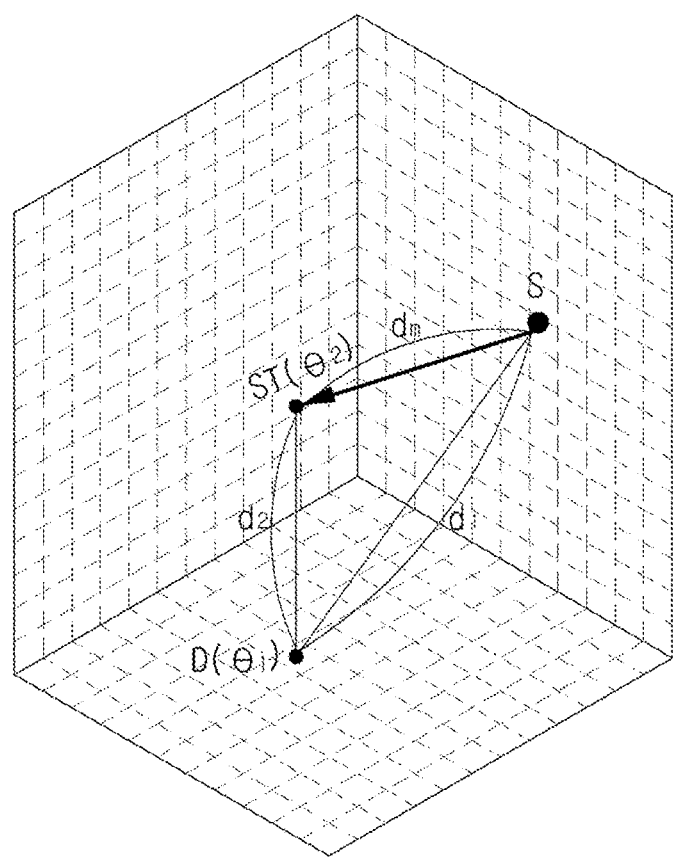
FIGS. 17A and 17B are views illustrating a screen displaying a position information image generated by an image generator according to an exemplary embodiment.
Figure 17B:
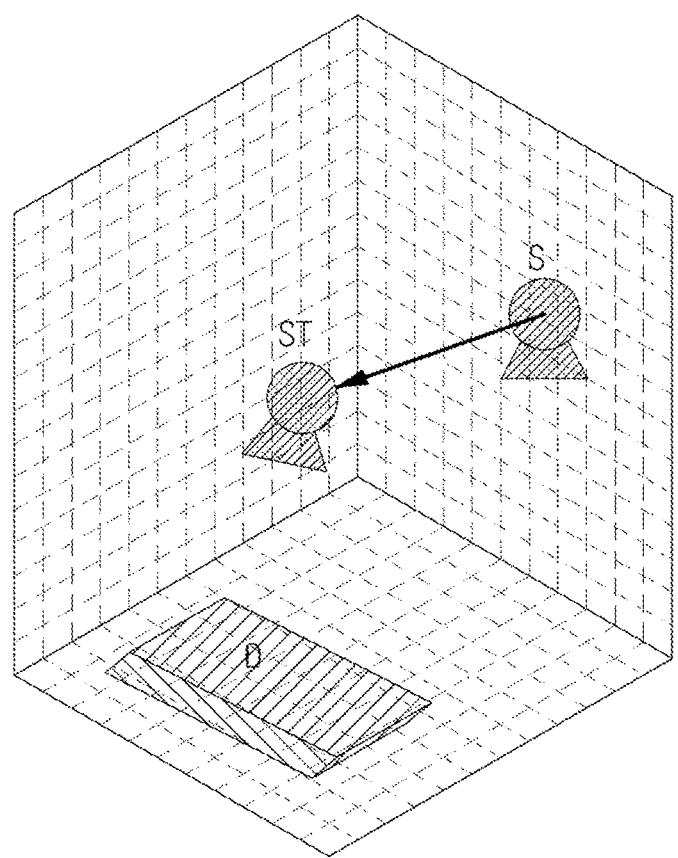

FIGS. 17A and 17B are views illustrating a position information image generated by the image generator 241 according to an exemplary embodiment.

Referring to FIG. 17A, the position information image may respectively represent relative positions of the X-ray source 210 and the X-ray detector 220 and the target position of the X-ray source 210 as points (S, D, ST) on the 3D coordinate system. Moreover, information regarding a current distance $d_1$, target distance $d_2$ and angle $\theta_1$ of the X-ray source 210 relative to the X-ray detector 220, and a displacement $d_m$ and target relative angle $\theta_2$ of the X-ray source 210 may be quantitatively represented. Kinds and representation methods of information included in the position information image are not limited.

Referring to FIG. 17B, the position information image may be displayed as an icon or an avatar to intuitively show the X-ray source 210 and the X-ray detector 220 to represent, in 3D space, information regarding the current position of the X-ray source 210 relative to the X-ray detector 220 and the target position of the X-ray source 210 with respect to the X-ray detector 220.

Figure 18:
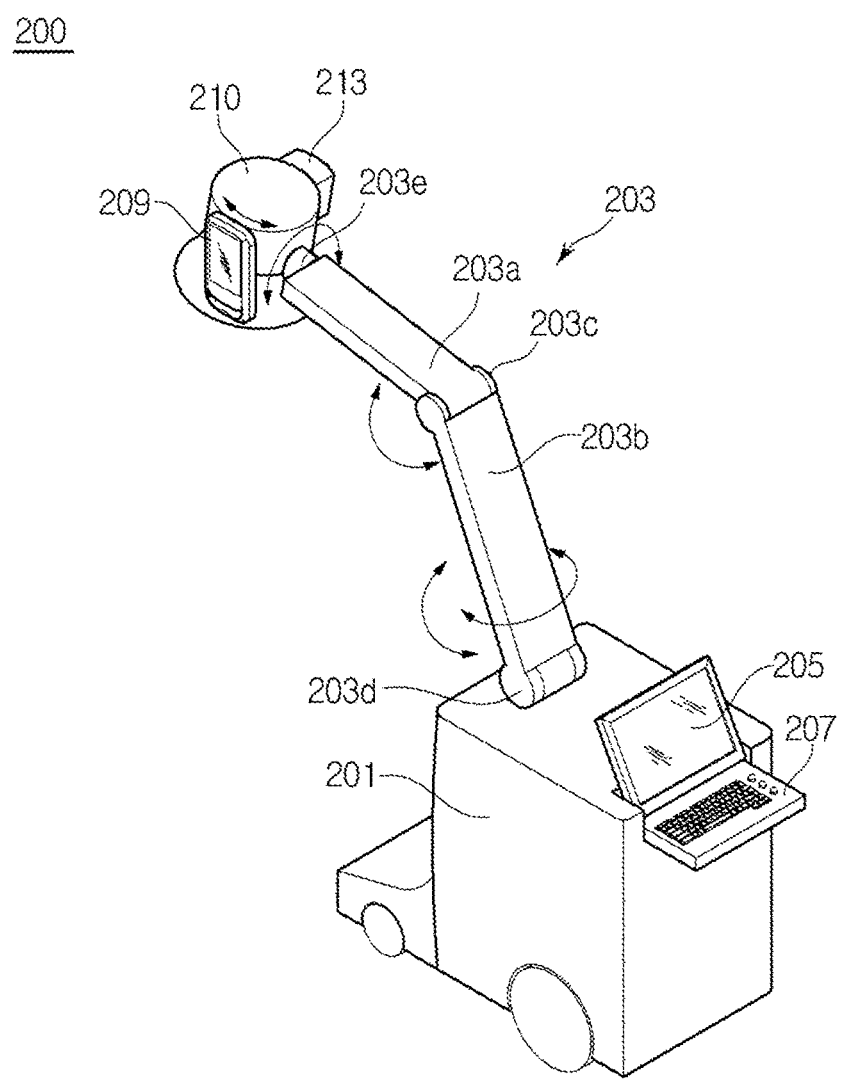
FIG. 18 is an exterior view of an image output unit to output the position information image according to an exemplary embodiment.

FIG. 18 is an exterior view of the image output unit 242 to output the position information image according to an exemplary embodiment.

Referring to FIG. 18, the exterior view of the mobile X-ray imaging apparatus 200 is the same as that of the mobile X-ray imaging apparatus 100 according to previous exemplary embodiments, except that the X-ray source 210 includes a panel 209. Thus, the illustrated elements of the mobile X-ray imaging apparatus 200 are the same as those of the mobile X-ray imaging apparatus 100.

The image output unit 242 to display a position information image may be implemented as a display unit 205 installed at a main body 201 or as the panel 209 separately installed at the X-ray source 210. A user may input control commands to a driving unit to drive a support arm 203 via an input unit 207 while viewing a position information image displayed on the display unit 205 or may directly move the X-ray source 210 while viewing a position information image displayed on the panel 209. Assuming that the determination of whether a control amount for moving the X-ray source 210 is automatically or manually performed, and the determination of whether the inputting of control commands is automatically or manually performed, is determined in accordance with whether a system or used performs the operations, respectively, a case in which a user inputs control commands to the driving unit via the input unit 107 may be viewed as the manual implementation for moving the X-ray source 210.

In addition, the position information acquisition unit 230 and the position information supply unit 240 may receive feedback for movement of the X-ray source 210 by a user. That is, when a user moves the X-ray source 210, position information acquiring performed by the position information acquisition unit 230 and position information supplying performed by the position information supply unit 240 are newly performed by reflecting changes in relative position information according to the movement of the X-ray source 210. The position information acquiring performed by the position information acquisition unit 230 and the position information supplying performed by the position information supply unit 240 may be performed periodically at certain periods of time or in real time and performed when the movement of the X-ray source 210 is sensed or a separate command is input by a user.

When the acquiring and supplying of the position information are performed periodically at certain periods of time, the position information image as illustrated in FIGS. 17A and 17B may be refreshed at each of the certain periods of time. On the other hand, when the acquiring and supplying of the position information are performed in real time, the position information image may be displayed as a live image.

Figure 19:
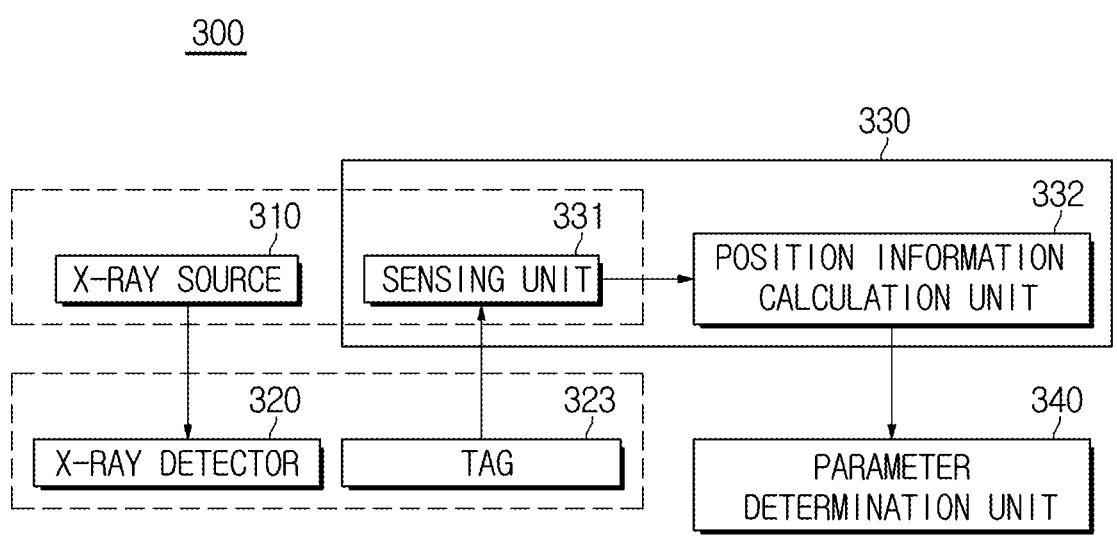
FIG. 19 is a control block diagram illustrating a mobile X-ray imaging apparatus according to another exemplary embodiment.

FIG. 19 is a control block diagram illustrating a mobile X-ray imaging apparatus 300 according to another exemplary embodiment.

Referring to FIG. 19, the mobile X-ray imaging apparatus 300 according to another exemplary embodiment includes an X-ray source 310 to generate X-rays and irradiate an object with the generated X-rays, an X-ray detector 320 to detect X-rays having passed through the object, a position information acquisition unit 330 to acquire position information of the X-ray source 310 relative to the X-ray detector 320, and a parameter determination unit 340 (e.g., parameter determiner) to determine an image parameter applied to X-ray imaging based on the position information of the X-ray source 310 relative to the X-ray detector 320.

The X-ray source 310, the X-ray detector 320, and the position information acquisition unit 330 are the same as those of the mobile X-ray imaging apparatus 100 according to the above-described exemplary embodiments. Thus, the X-ray source 310 may be installed on a movable main body and may be movable in 3D space, and the X-ray detector 320 may be implemented as a portable X-ray detector.

In addition, in the mobile X-ray imaging apparatus 300 according to the present exemplary embodiment, a sensing unit 331 may also sense a position of each of the X-ray source 310 and the X-ray detector 320 from a third position, or the sensing unit 331 may be installed at the X-ray detector 320 and a tag 323 may be installed at the X-ray source 310. Alternatively, the sensing unit 331 may be installed at each of the X-ray source 310 and the X-ray detector 320 to sense the tag 323 at the third position. In the following discussion of the exemplary embodiment, a case in which the sensing unit 331 is installed at the X-ray source 310 to sense the tag 323 installed at the X-ray detector 320 will be described by way of example.

The present exemplary embodiment is different from the above-described exemplary embodiments in terms of acquisition time of position information used in the parameter determination unit 340. Relative position information used to determine an image parameter is not relative position information of the X-ray source 310 located at a certain position, but relative position information in a state in which the X-ray source 310 is moved to a position corresponding to the X-ray detector 320 to perform X-ray imaging. Movement of the X-ray source 310 may be performed by any one of the above-described two exemplary embodiments or may be intuitively performed by a user without a supply of position information.

The parameter determination unit 340 may determine an optimum image parameter using a distance, e.g., source to image distance (SID), and an angle of the X-ray source 310 relative to the X-ray detector 320. According to an exemplary embodiment, the image parameter may include at least one type of exposure parameters, for example, tube voltage, tube current, exposure time, kind and thickness of a filter, a target material of a positive electrode, a focal spot size, and the like, position and angle of a grid, and a field of view (FOV). Hereinafter, the image parameter determined by the parameter determination unit 340 will be described in detail.

Figure 20:
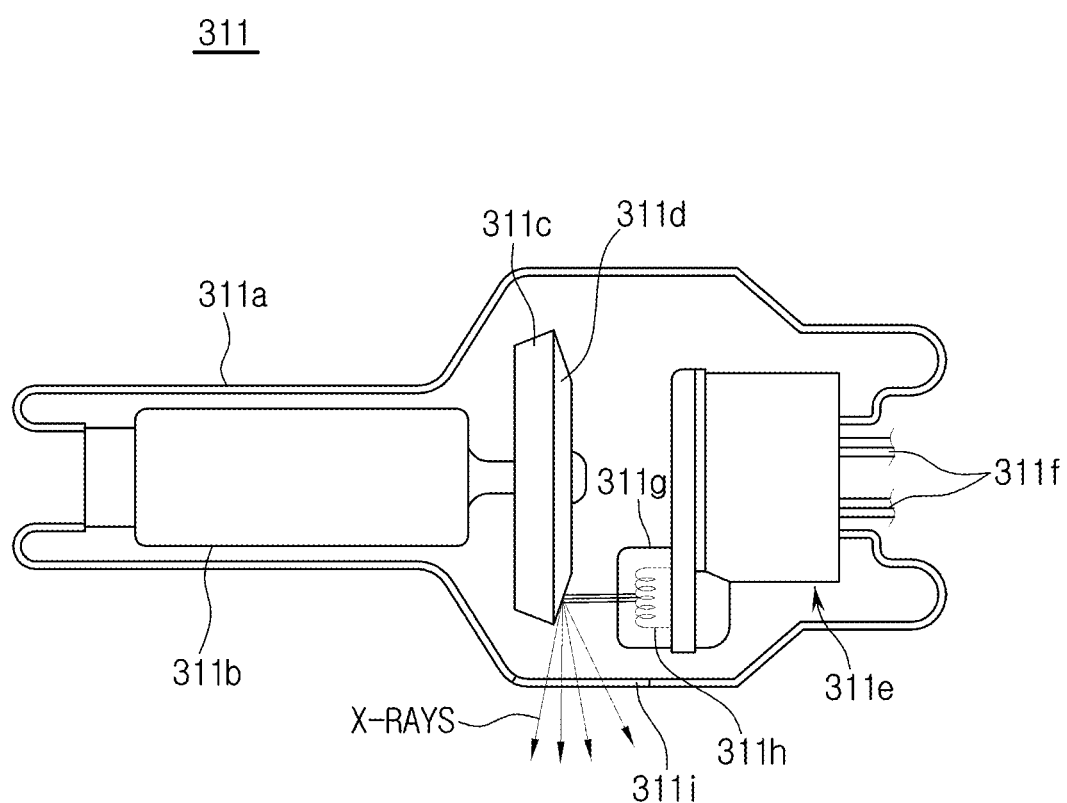
FIG. 20 is a view illustrating the configuration of an X-ray tube including an X-ray source to generate X-rays according to an exemplary embodiment.

FIG. 20 is a view illustrating the configuration of an X-ray tube 311 including an X-ray source to generate X-rays according to an exemplary embodiment.

The X-ray tube 311 may be implemented as a two-electrode vacuum tube including positive and negative electrodes 311c and 311e. The negative electrode 311e includes a filament 311h and a focusing electrode 311g to focus electrons. The focusing electrode 311g is also referred to as a focusing cup.

An interior of a glass tube 311a is evacuated to a high vacuum state of approximately 10 mmHg and the filament 311h of the negative electrode 311e is heated to a high temperature to generate thermal electrons. For example, the filament 311h may be made of tungsten and may be heated by applying current to an electric wire 311f connected to the filament 311h.

The positive electrode 311c is primarily made of copper, a target material 311d is coated or disposed at a side of the positive electrode 311c that faces the negative electrode 311e, and the target material 311d may be a high-resistance material such as Cr, Fe, Co, Ni, W, Mo, or the like. The target material 311d is tilted at a certain angle and, as a tilt angle increases, a focal spot size decreases. In addition, the focal spot size may vary according to tube voltage, tube current, the size of the filament 311h, the size of the focusing electrode 311g, and a distance between the positive and negative electrodes 311c and 311e.

When a high voltage is applied between the positive and negative electrodes 311c and 311e, thermal electrons accelerate and collide with the target material 311g of the positive electrode 311c, generating X-rays. The generated X-rays are emitted to the outside via a window 311i, and the window 311i may be made of a beryllium (Be) thin film. In this regard, a filter may be positioned at a front or rear surface of the window 311i to filter X-rays having a particular energy band.

The target material 311d may be rotated by a rotor 311b and, when the target material 311d is rotated, the heat capacity per unit area may be 10 times or more than when the target material 311d is in a fixed state and the focal spot size decreases.

A voltage applied between the negative and positive electrodes 311e and 311c of the X-ray tube 311 is referred to as tube voltage, and the magnitude of the voltage may be represented in peak kilovolts (kVp). As the tube voltage increases, a velocity of thermal electrons is increased and, consequently, the thermal electrons collide with the target material 311d. As a result, the energy of X-rays (energy of photons) is increased. Current flowing in the X-ray tube 311 is referred to as tube current and may be represented as mean amperage (mA). When the tube current is increased, the number of thermal electrons released from the filament 311h is increased and, consequently, the thermal electrons collide with the target material 311d, thereby increasing a dose of the generated X-rays (the number of X-ray photons).

Accordingly, the energy of X-rays may be controlled by tube voltage, and the intensity or dose of X-rays may be controlled by tube current and X-ray exposure time. More particularly, when emitted X-rays have a certain energy band, the energy band may be defined by an upper limit and a lower limit. The upper limit of the energy band, e.g., the maximum energy of emitted X-rays, may be controlled by the magnitude of tube voltage, and the lower limit of the energy band, e.g., the minimum energy of emitted X-rays, may be controlled by a filter. The average energy of emitted X-rays may be increased by filtering X-rays having a low energy band through a filter.

The parameter determination unit 340 may determine an optimum exposure parameter in consideration of a distance between the X-ray source 310 and the X-ray detector 320 and dose conditions such as dose area product (DAP), entrance skin dose (ESD), and the like.

Figure 21:
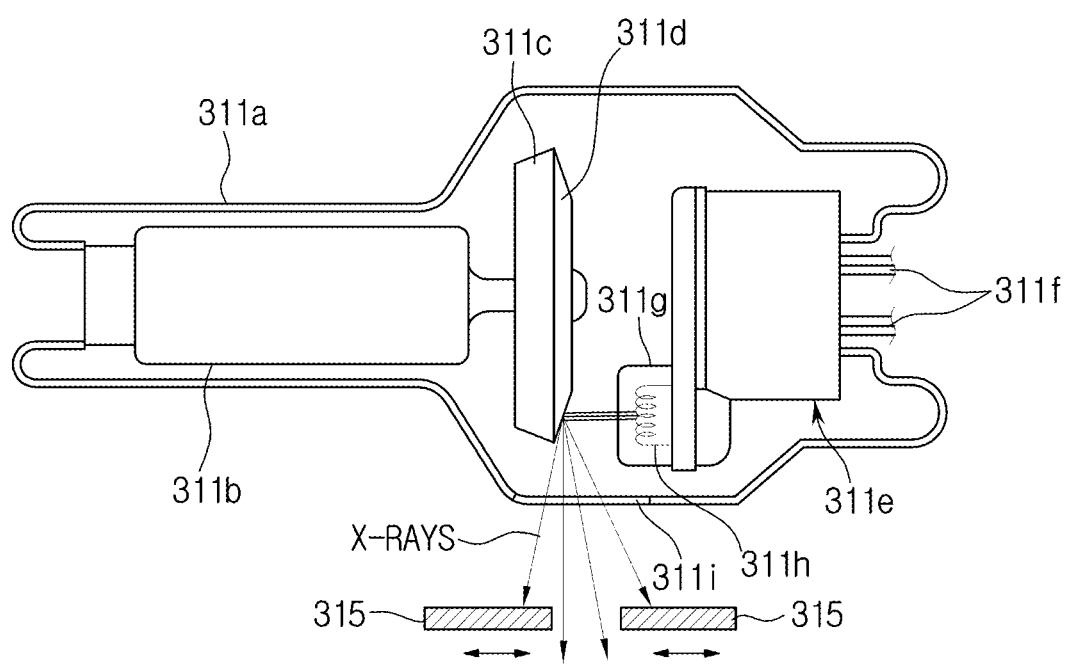
FIG. 21 is a view illustrating a structure of a collimator to adjust a radiation field of X-rays according to an exemplary embodiment.
Figure 22:
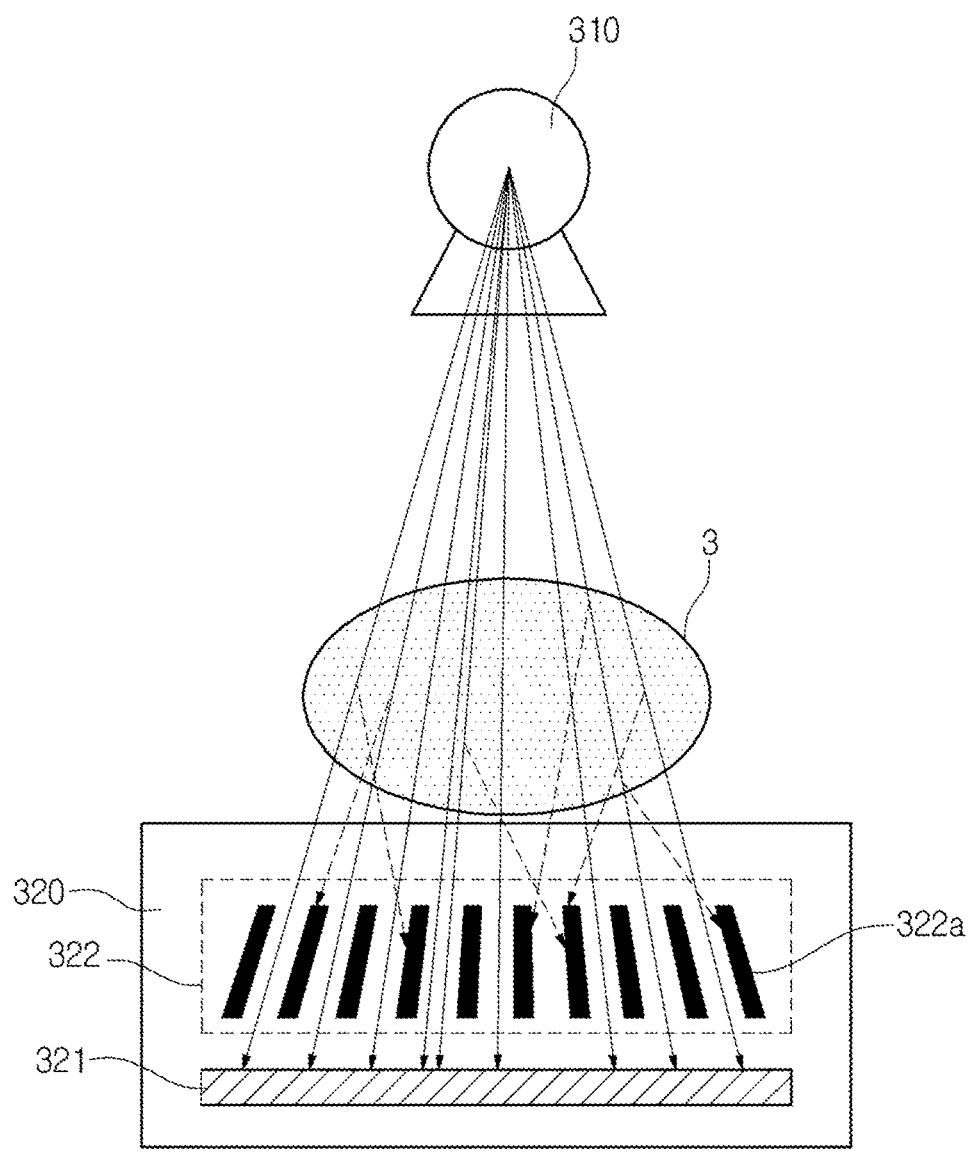
FIG. 22 is a view illustrating a structure of a grid to control scattered X-rays according to an exemplary embodiment.

FIG. 21 is a view illustrating a structure of a collimator 315 to adjust a radiation field of X-rays according to an exemplary embodiment. FIG. 22 is a view illustrating a structure of a grid to control scattered X-rays according to an exemplary embodiment.

Referring to FIG. 21, the collimator 315 may be positioned at a front surface of the window 311i of the X-ray tube 311 to adjust the radiation field of X-rays. That is, the FOV of X-rays may be adjusted using the collimator 315. The collimator 315 may include a plurality of blades formed of an X-ray absorbing material, and the radiation field of X-rays may be adjusted by moving the blades and thereby absorbing the X-rays. In addition, when the radiation field of X-rays is decreased, the amount of scattered X-rays may be reduced. The parameter determination unit 340 determines an optimum X-ray radiation field based on at least one selected from a distance between the X-ray source 310 and the X-ray detector 320, an angle of the X-ray source 310 relative to the X-ray detector 320, and a tilt angle of the X-ray source 310.

Referring to FIG. 22, some of the X-rays emitted from the X-ray source 310 may be scattered by deviating from an original path as a result of colliding with dust particles in the air or another object as the emitted X-rays proceed towards the X-ray detector 320. When the scattered X-rays are incident upon the X-ray detector 320, an X-ray image is adversely affected, resulting in deterioration of quality of the X-ray image, e.g., reduction in contrast of the X-ray image, or the like.

Thus, the X-ray detector 320 includes a grid 322 which absorbs the scattered X-rays and is disposed at a front end of a detection module 321 to detect X-rays. The grid 322 has a structure in which a shielding material 322a to absorb X-rays, such as lead (Pb), is arranged. When the emitted X-rays proceed in an original direction, e.g., a straight direction, the X-rays pass through the shielding material 322a and are incident upon the detection module 321, and the scattered X-rays collide with the shielding material 322a to be absorbed thereby.

As illustrated in FIG. 22, the shielding material 322a may be arranged in a linear form or as a cross structure. In addition, as illustrated in FIG. 22, the shielding material 322a may be tilted towards an X-ray emission direction and arranged as a focusing type device or a material which is parallel to the X-ray emission direction.

Although not shown in FIG. 22, the X-ray detector 320 may include a driving unit capable of mechanically moving the grid 322. The driving unit includes a motor and a drive. Thus, an angle or central position of the grid 322 may be adjusted by transmitting a control signal to the driving unit from the outside.

When a direction of incident X-rays does not coincide with a direction of the grid 322, a cut-off phenomenon occurs, and thus the scattered X-rays are incident upon the detection module 321 or X-rays proceeding straight are absorbed by the shielding material 322a. To correct these problems, the direction of incident X-rays should be aligned with the direction of the grid 322, and the parameter determination unit 340 may determine an angle or central position of the grid 322 based on the position information of the X-ray source 310 relative to the X-ray detector 320.

Figure 23:
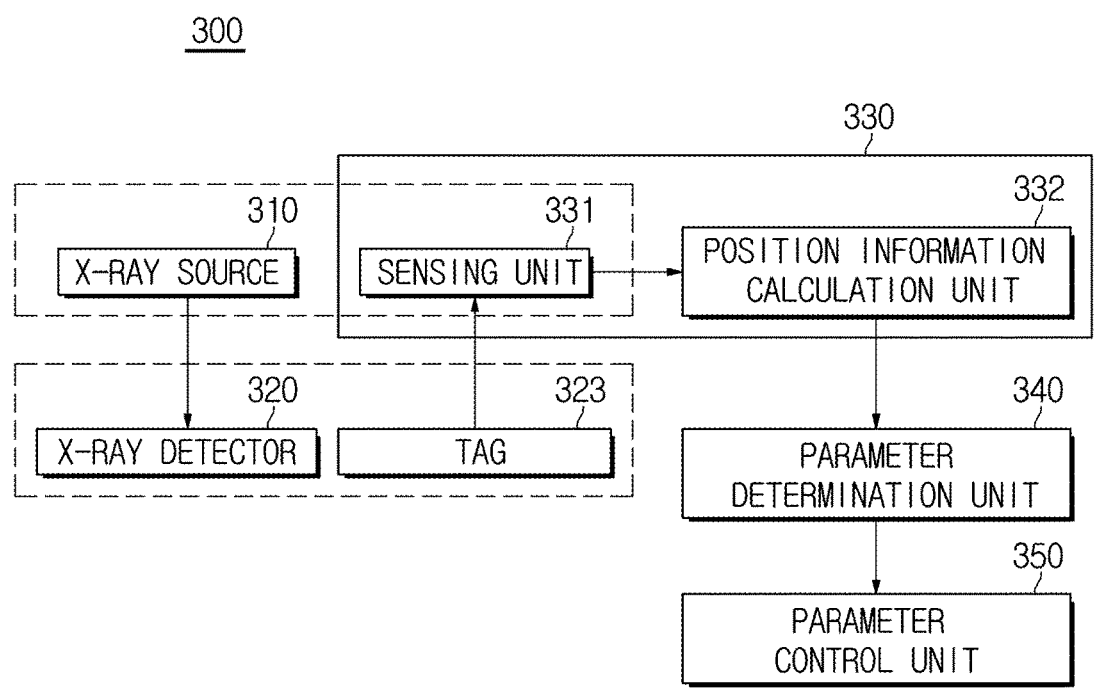
FIG. 23 is a control block diagram illustrating a mobile X-ray imaging apparatus that automatically controls an image parameter according to an exemplary embodiment.

FIG. 23 is a control block diagram illustrating the mobile X-ray imaging apparatus 300 that automatically controls an image parameter according to an exemplary embodiment.

When the parameter determination unit 340 determines an optimum image parameter, a user may directly control an image parameter based thereon, or the mobile X-ray imaging apparatus 300 may automatically control the image parameter. In the latter case, as illustrated in FIG. 23, the mobile X-ray imaging apparatus 300 may further include a parameter control unit 350 (e.g., parameter controller) to automatically control the image parameter according to determination results of the parameter determination unit 340.

The parameter control unit 350 may control tube voltage and tube current supplied to the X-ray tube 311 of the X-ray source 310, an X-ray exposure time, a focal spot size, type and thickness of a filter, and a positive electrode target material. In addition, the parameter control unit 350 may control the radiation field of X-rays by transmitting a control signal to a driving unit to drive the collimator 315 and control an angle or central position of the grid 322 by transmitting a control signal to a driving unit to drive the grid 322.

According to another exemplary embodiment, a user may manually adjust some of the parameters according to the structure of the mobile X-ray imaging apparatus 300, and other of the parameters may be automatically adjusted by the parameter control unit 350.

Hereinafter, exemplary embodiments of a method of controlling the mobile X-ray imaging apparatus according to one of the exemplary embodiments will be described in detail.

Figure 24:
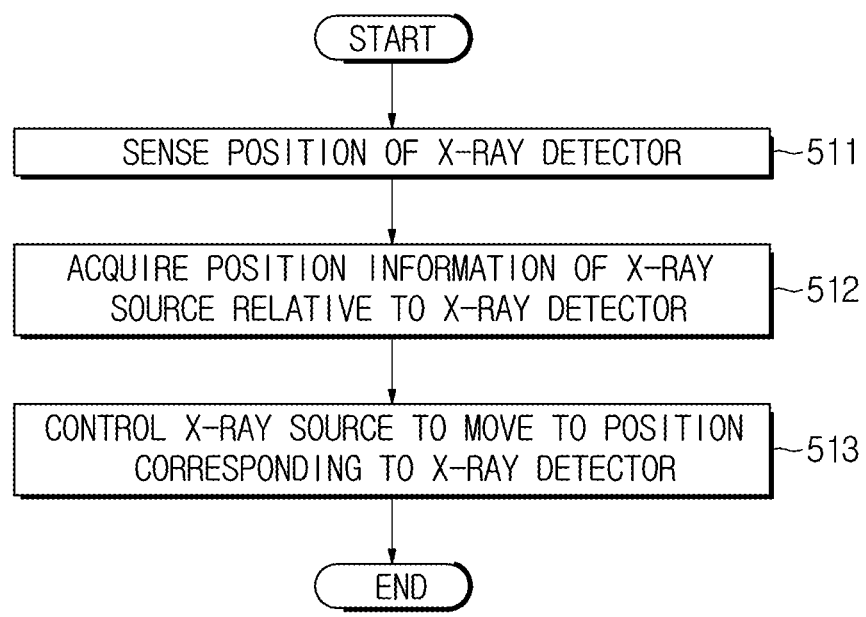
FIG. 24 is a flowchart illustrating a mobile X-ray imaging apparatus control method according to an exemplary embodiment.

FIG. 24 is a flowchart illustrating a mobile X-ray imaging apparatus control method according to an exemplary embodiment. In the present exemplary embodiment, the mobile X-ray imaging apparatus 100 according to the above-described exemplary embodiment may be used to perform the exemplary method shown in FIG. 24, although it is understood that the exemplary method shown in FIG. 24 may also be performed by other apparatuses.

Referring to FIG. 24, first, a position of the X-ray detector 120 is sensed at operation 511. The X-ray detector 120 may be a portable X-ray detector, and the position of the X-ray detector 120 may be sensed after positioning the X-ray detector 120 at a particular position, to perform X-ray imaging. Sensing of the position of the X-ray detector 120 may include sensing the tag 123 installed at the X-ray detector 120 by the sensing unit 131 installed at the X-ray source 110, sensing the tags 123-1 and 123-2 respectively installed at the X-ray source 110 and the X-ray detector 120 by the sensing unit 131 at a third position, sensing the tag 123 installed at the X-ray source 110 by the sensing unit 131 installed at the X-ray detector 120, or sensing the tag 123 at a third position by the sensing unit 131 installed at each of the X-ray source 110 and the X-ray detector 120. To more accurately sense the position, the tags 123 or the sensing units 131 may be respectively installed at multiple positions of the X-ray detector 120, e.g., three or four corners of the X-ray detector 120.

Based on the sensing results of the position of the X-ray detector 120, position information of the X-ray source 110 relative to the X-ray detector 120 is acquired at operation 512. The relative position information includes a distance between the X-ray detector 120 and the X-ray source 110 and angle information of the X-ray source 110 relative to the X-ray detector 120. In addition, to acquire the position information of the X-ray source 110 relative to the X-ray detector 120, the position of the X-ray source 110 also should be sensed. For example, the position of the X-ray source 110 may be separately sensed by the tag 123 or the sensing unit 131 located at a third position, or the sensing unit 131 or the tag 123 to sense the position of the X-ray detector 120 may be installed at the X-ray source 110 and the position of the X-ray detector 120 may be sensed without separate sensing of the position of the X-ray source 110 so that the relative position information is acquired.

Based on the acquired relative position information, the X-ray source 110 is controlled to move to a position corresponding to the X-ray detector 120 at operation 513. In this regard, the X-ray detector 120 is located at a position for performing X-ray imaging, and the X-ray source 110 is controlled to move to the position corresponding to the X-ray detector 120 from an arbitrary position in 3D space, based on the relative position information. The position of the X-ray source 110 corresponding to the X-ray detector 120 may be pre-stored as a default or calculated by a separate algorithm. The latter case will be described below.

Figure 25:
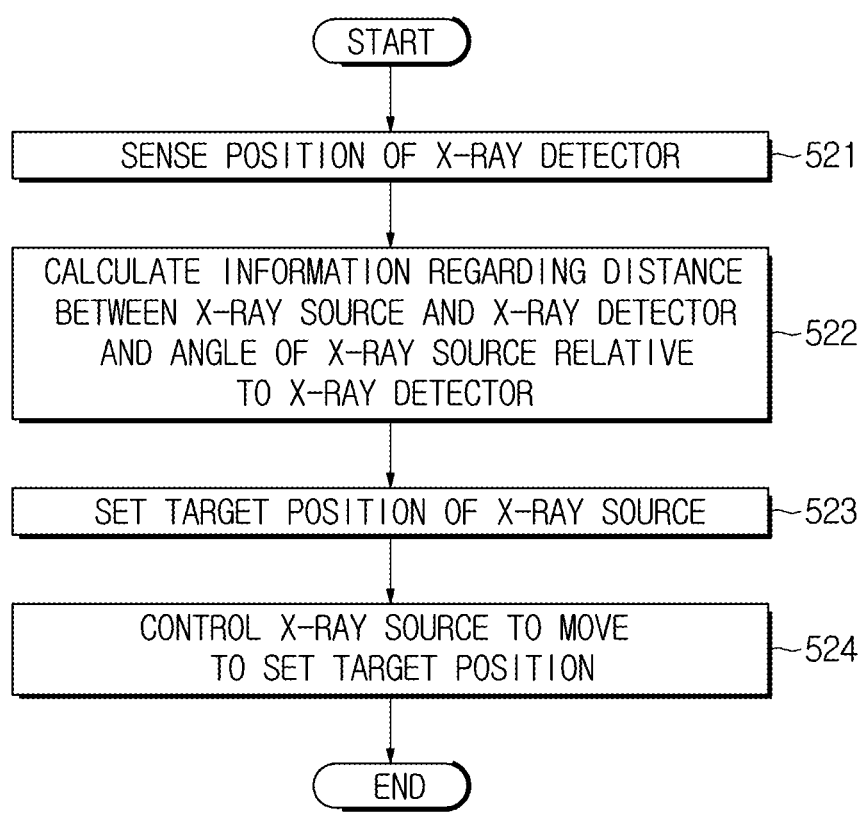
FIG. 25 is a flowchart illustrating a mobile X-ray imaging apparatus control method according to an exemplary embodiment in which a position of an X-ray source is set.

FIG. 25 is a flowchart illustrating a mobile X-ray imaging apparatus control method according to an exemplary embodiment of the present invention in which the position of the X-ray source 110 is set.

Referring to FIG. 25, the position of the X-ray detector 120 is sensed at operation 521, and information regarding a distance between the X-ray source 110 and the X-ray detector 120 and an angle of the X-ray source 110 relative to the X-ray detector 120 is calculated at operation 522.

Subsequently, a target position of the X-ray source 110 is set at operation 523. The target position of the X-ray source 110, which is as described above as the position of the X-ray source 110 corresponding to the X-ray detector 120, is a position of the X-ray source 110 relative to the X-ray detector 120 and may be defined by a distance between the X-ray source 110 and the X-ray detector 120 and an angle of the X-ray source 110 relative to the X-ray detector 120. An optimum distance between the X-ray source 110 and the X-ray detector 120 and an X-ray incident angle may vary according to a site of an object to be X-ray imaged, conditions of the object, intended purposes of the X-ray images, or the like. Thus, an algorithm for setting the target position of the X-ray source 110 according to several variables may be pre-stored and, when information corresponding to the variables is input, the target position of the X-ray source 110 may be set according to the pre-stored algorithm.

When the target position of the X-ray source 110 is set, the X-ray source 110 is controlled to move to the set target position at operation 524. In particular, a control amount for moving the X-ray source 110 to the target position from the current position is calculated, and a control signal corresponding to the control amount is transmitted to the driving unit 150 to drive movement of the X-ray source 110.

Figure 26:
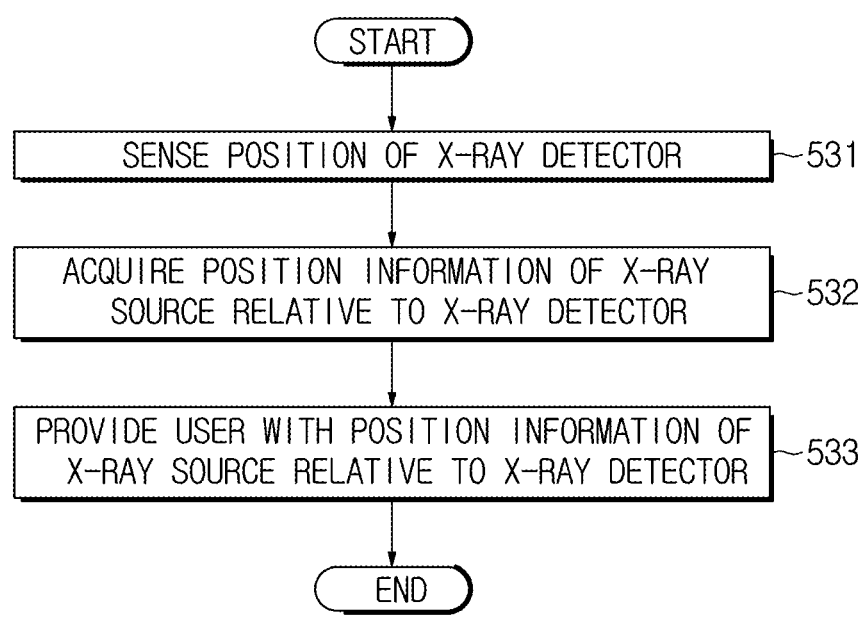
FIG. 26 is a flowchart illustrating a mobile X-ray imaging apparatus control method according to another exemplary embodiment.

FIG. 26 is a flowchart illustrating a mobile X-ray imaging apparatus control method according to another exemplary embodiment. In the present exemplary embodiment, the mobile X-ray imaging apparatus 200 according to the above-described exemplary embodiment may be used to perform the exemplary method shown in FIG. 26, although it is understood that the exemplary method shown in FIG. 26 may also be performed by other apparatuses.

Referring to FIG. 26, first, the position of the X-ray detector 220 is sensed at operation 531, and position information of the X-ray source 210 relative to the X-ray detector 220 is acquired at operation 532. Descriptions of these operations have already been provided in the above-described exemplary embodiment.

Subsequently, the position information of the X-ray source 210 relative to the X-ray detector 220 is provided to a user at operation 533. A method of providing a user with the relative position information is not limited to any particular type of method, and the relative position information itself may be quantitatively provided, or information which is processed in such a way as to enable a user to easily identify the relative position information may be provided. In addition, the position information may be visually or audibly provided, and information regarding the target position of the X-ray source 210 may also be provided together with the relative position information. When the relative position information is provided, a user may identify the current position relationship between the X-ray detector 220 and the X-ray source 210 and directly move the X-ray source 210 to a position corresponding to the X-ray detector 220.

Figure 27:
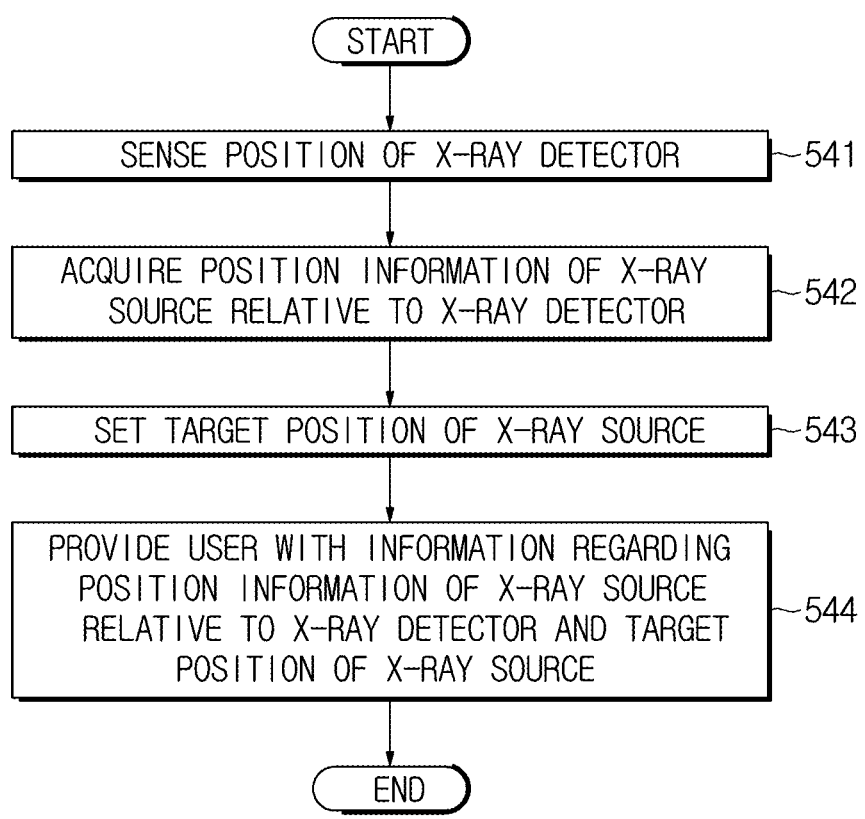
FIG. 27 is a flowchart illustrating a mobile X-ray imaging apparatus control method according to another exemplary embodiment in which information regarding a target position of the X-ray source is provided.

FIG. 27 is a flowchart illustrating a mobile X-ray imaging apparatus control method according to another exemplary embodiment in which information regarding the target position of the X-ray source 210 is provided.

Referring to FIG. 27, the position of the X-ray detector 220 is sensed at operation 541), and position information of the X-ray source 210 relative to the X-ray detector 220 is acquired at operation 542.

Subsequently, the target position of the X-ray source 210 is set at operation 543. As described above, an algorithm for setting the target position of the X-ray source 210 according to several variables may be pre-stored and, when information corresponding to the variables is input, the target position of the X-ray source 210 may be set according to the pre-stored algorithm.

The position information of the X-ray source 210 relative to the X-ray detector 220 and the target position of the X-ray source 210 are provided to a user at operation 544. For example, when a position information image including the two pieces of information (the relative position information and the target position) is generated and provided, the generated position information image may be displayed, for example, on the panel 209 or display unit 205 illustrated in FIG. 18, and a user may control the position of the X-ray source 210 while viewing the position information image.

Figure 28:
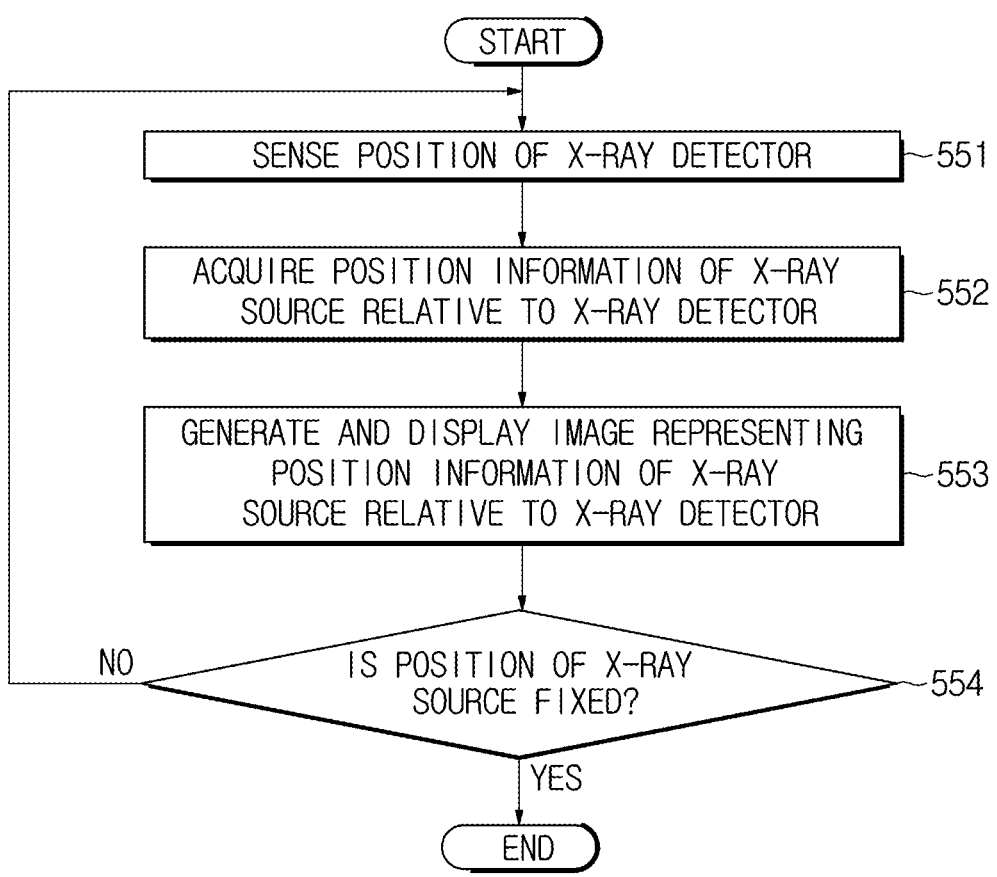
FIG. 28 is a flowchart illustrating a mobile X-ray imaging apparatus control method according to another exemplary embodiment in which movement of the X-ray source is received as feedback.

FIG. 28 is a flowchart illustrating a mobile X-ray imaging apparatus control method according to another exemplary embodiment in which movement of the X-ray source 210 is received as feedback.

Referring to FIG. 28, the position of the X-ray detector 220 is sensed at operation 551, and position information of the X-ray source 210 relative to the X-ray detector 220 is acquired at operation 552.

Subsequently, a position information image representing the position information of the X-ray source 210 relative to the X-ray detector 220 is generated and displayed at operation 553. The position information image may represent target position information of the X-ray source 210, and the target position information of the X-ray source 210 may be set by the pre-stored algorithm.

When the position information image is displayed, a user may then manually move the X-ray source 210 based on the displayed position information image. When the position of the X-ray source 210 is not fixed (No in operation 554), operations 551 to 553 are repeated. That is, the movement of the X-ray source 210 may be received as feedback, and the series of operations may be performed periodically at certain periods of time or in real time. When the operations are performed in real time, the position information image is displayed as a live image. Alternatively, the movement of the X-ray source 210 may be determined and when the movement of the X-ray source 210 is input, the operations of sensing the position of the X-ray detector 220 at operation 551 through generating and displaying the position information image at operation 553 may be repeated or, when a separate command is input by a user, operations 551 to 553 may be repeated.

Figure 29:
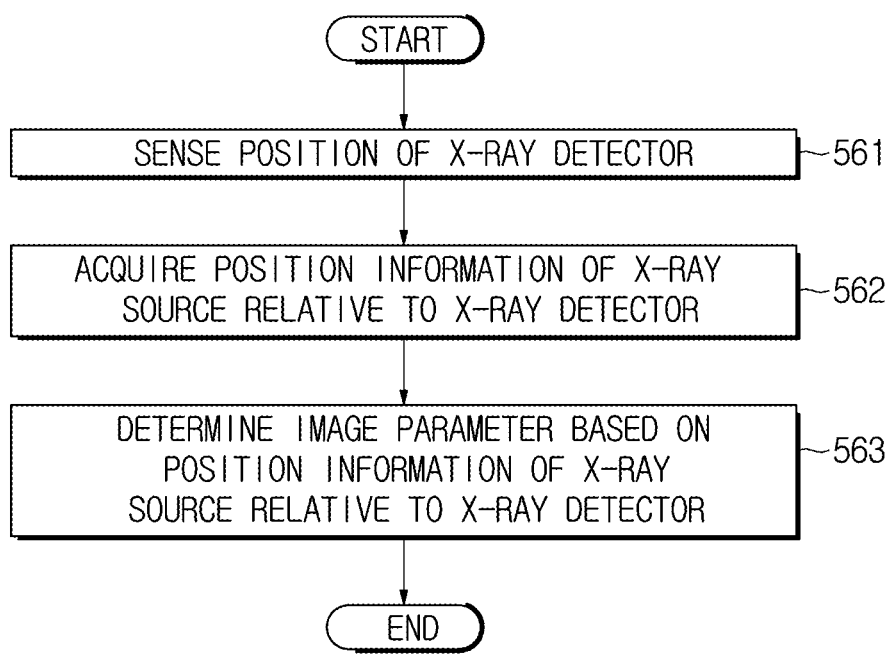
FIG. 29 is a flowchart illustrating a mobile X-ray imaging apparatus control method according to another exemplary embodiment.

FIG. 29 is a flowchart illustrating a mobile X-ray imaging apparatus control method according to another exemplary embodiment. In the present exemplary embodiment, the mobile X-ray imaging apparatus 300 according to the above-described exemplary embodiment may be used to perform the exemplary method shown in FIG. 29, although it is understood that the exemplary method shown in FIG. 29 may also be performed by other apparatuses.

Referring to FIG. 29, when the X-ray detector 220 and the X-ray source 210 are located at positions for performing X-ray imaging, the position of the X-ray detector 220 is sensed at operation 561, and position information of the X-ray source 210 relative to the X-ray detector 220 is acquired at operation 562.

An image parameter applied for X-ray imaging is determined based on the position information of the X-ray source 210 relative to the X-ray detector 220 at operation 563. According to an exemplary embodiment, the image parameter includes at least one type of exposure parameters, for example, tube voltage, tube current, exposure time, kind and thickness of a filter, a target material of a positive electrode, a focal spot size, and the like, and diffusion parameters such as an angle or central position of a grid, FOV, and the like. In addition, an optimum exposure parameter and diffusion parameter may be determined in consideration of dose conditions such as DAP and ESD together with the distance between the X-ray source 310 and the X-ray detector 320 and angle information of the X-ray source 310 relative to the X-ray detector 220.

When the image parameter is determined, a user may manually control the image parameter. Alternatively, control of the image parameter may be automatically performed in a system or performed manually and automatically in combination.

Figure 30:
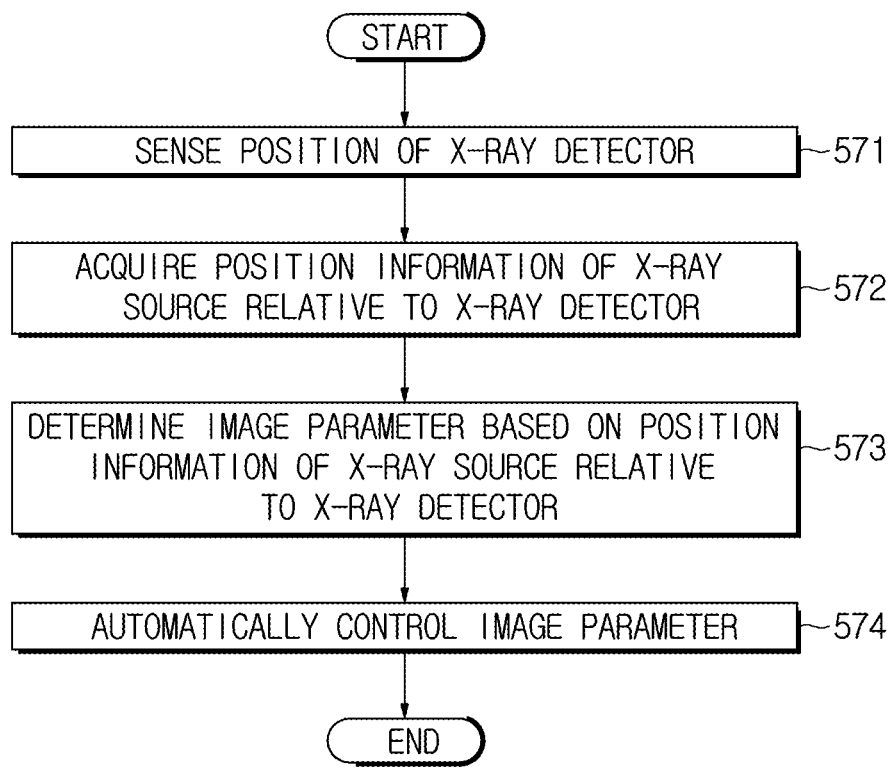
FIG. 30 is a flowchart illustrating a mobile X-ray imaging apparatus control method according to another exemplary embodiment in which an image parameter is automatically controlled.

FIG. 30 is a flowchart illustrating a mobile X-ray imaging apparatus control method according to another exemplary embodiment in which the image parameter is automatically controlled.

Referring to FIG. 30, when the X-ray detector 320 and the X-ray source 310 are located at positions for performing X-ray imaging, the position of the X-ray detector 320 is sensed at operation 571), and position information of the X-ray source 310 relative to the X-ray detector 320 is acquired at operation 572.

An image parameter applied for X-ray imaging is determined based on the position information of the X-ray source 310 relative to the X-ray detector 320 at operation 573. The image parameter includes at least one type of exposure parameters, for example, tube voltage, tube current, exposure time, kind and thickness of a filter, a target material of a positive electrode, a focal spot size, and the like, and diffusion parameters such as an angle or central position of a grid, FOV, and the like.

Subsequently, the image parameter is automatically controlled according to determination results at operation 574. In particular, tube voltage and tube current, X-ray exposure time, and a FOV of X-rays may be automatically controlled, and type and thickness of a filter, a positive electrode target material, a focal spot size, and an angle or central position of a grid may also be automatically controlled according to the structure of the mobile X-ray imaging apparatus 300.

As is apparent from the above description, position information indicating a position of an X-ray source relative to a portable X-ray detector located in an arbitrary space may be identified, and the position of the X-ray source may be automatically controlled based on the identified relative position information, or alternatively, the relative position information may be provided to a user, thereby increasing accuracy of position alignment between the X-ray source and the X-ray detector.

In addition, image parameters applied for X-ray imaging may be determined based on the identified relative position information, thereby achieving an X-ray exposure amount which may be effectively controlled and obtaining an excellent image quality.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. A mobile X-ray imaging apparatus comprising:
a movable main body;
an X-ray source installed on the main body via an arm, at least one from among a tilt angle and a rotation angle of the arm being adjustable;
a portable X-ray detector configured to detect X-rays emitted from the X-ray source;
a position information acquirer configured to acquire position information indicating a position of the X-ray source relative to the portable X-ray detector; and
a controller configured to control the X-ray source to move to a position corresponding to the portable X-ray detector based on the position information, and configured to determine a combination of two different types of image parameters to be applied during X-ray imaging based on the position information indicating the position of the X-ray source relative to the portable X-ray detector when the X-ray source and the portable X-ray detector are located at positions for the X-ray imaging,
wherein one of the image parameters comprises a type and a thickness of a filter used to filter X-rays in a predetermined energy band, among the X-rays emitted by the X-ray source.

2. The mobile X-ray imaging apparatus according to claim 1, further comprising a tag installed on the portable X-ray detector,
wherein the position information acquirer comprises:
a sensor configured to sense the tag; and
a position information calculator configured to calculate the position information based on an output signal output by the sensor.

3. The mobile X-ray imaging apparatus according to claim 2, wherein the sensor is installed on the X-ray source.

4. The mobile X-ray imaging apparatus according to claim 2, further comprising a tag installed on the X-ray source,
wherein the sensor is located in an area comprising the X-ray source and the portable X-ray detector and further senses the tag installed at the X-ray source.

5. The mobile X-ray imaging apparatus according to claim 1, further comprising a tag located in an area comprising the X-ray source and the portable X-ray detector,
wherein the position information acquirer comprises:
a sensor configured to sense the tag; and
a position information calculator configured to calculate the position information based on an output signal of the sensor.

6. The mobile X-ray imaging apparatus according to claim 2, wherein the position information comprises information regarding a distance between the X-ray source and the portable X-ray detector and information regarding an angle of the X-ray source relative to the portable X-ray detector,
wherein the mobile X-ray imaging apparatus further comprises a driving mechanism configured to drive the arm,
wherein the controller is configured to transmit, to the driving mechanism, a control signal corresponding to a control amount to be used for moving the X-ray source to a position corresponding to the portable X-ray detector,
wherein the mobile X-ray imaging apparatus further comprises a position setter configured to set a position of the X-ray source corresponding to the portable X-ray detector, and
wherein the controller is configured to control a tilt angle of the X-ray source according to the set position of the X-ray source corresponding to the portable X-ray detector.

7. A method of controlling a mobile X-ray imaging apparatus comprising an X-ray source installed on a movable main body via an arm, a tilt angle and rotation angle of the arm being adjustable, and a portable X-ray detector configured to detect X-rays emitted from the X-ray source, the method comprising:
sensing a position of the portable X-ray detector;
acquiring position information indicating a position of the X-ray source relative to the portable X-ray detector based on sensing results of the sensing;
controlling the X-ray source to move to a position corresponding to the portable X-ray detector based on the acquired position information; and
determining a combination of two different types of image parameters to be applied during X-ray imaging based on the position information indicating the position of the X-ray source relative to the portable X-ray detector when the X-ray source and the portable X-ray detector are located at positions for the X-ray imaging, wherein one of the image parameters comprises a type and a thickness of a filter used to filter X-rays in a predetermined energy band, among the X-rays emitted by the X-ray source.

8. The method according to claim 7, wherein the sensing comprises sensing a tag installed on the portable X-ray detector or the X-ray source or located in an area comprising the portable X-ray detector and the X-ray source.

9. The method according to claim 7, wherein the acquiring comprises calculating a distance between the X-ray source and the portable X-ray detector and an angle of the X-ray source relative to the portable X-ray detector based on the sensing results, wherein the method further comprises setting the position corresponding to the portable X-ray detector, the position corresponding to the portable X-ray detector being defined by a distance between the X-ray source and the portable X-ray detector and an angle of the X-ray source relative to the portable X-ray detector, wherein the controlling comprises:

calculating a control amount for moving the X-ray source to the position corresponding to the portable X-ray detector based on the acquired position information and the set position corresponding to the portable X-ray detector; and transmitting a control signal corresponding to the control amount to a driving unit to drive the arm such that the X-ray source moves to the position corresponding to the portable X-ray detector, and wherein the method further comprises controlling a tilt angle of the X-ray source according to the position corresponding to the portable X-ray detector.

10. The mobile X-ray imaging apparatus according to claim 1, wherein the position information comprises information regarding a distance between the X-ray source and the portable X-ray detector.

11. The mobile X-ray imaging apparatus according to claim 1, wherein the position information comprises information regarding an angle of the X-ray source relative to the portable X-ray detector.

12. The mobile X-ray imaging apparatus according to claim 1, wherein the controller is configured to determine the other image parameter among the two different types of image parameters as at least one of a tube voltage and a tube current supplied to the X-ray source, and an X-ray exposure time, based on the position information.

13. The mobile X-ray imaging apparatus according to claim 1, wherein the controller is configured to automatically control the other image parameter among the two different types of image parameters, the other image parameter comprising at least one of a tube voltage, a tube current, and an X-ray exposure time, based on the position information.

* * * * *